(12) United States Patent
Dianzani et al.

(10) Patent No.: US 12,263,204 B2
(45) Date of Patent: Apr. 1, 2025

(54) ANTI-TUMOR THERAPEUTIC AGENTS BASED ON B7h RECEPTOR LIGANDS

(71) Applicants: Università degli Studi del Piemonte Orientale "Amedeo Avogadro", Vercelli (IT); Novaicos S.r.l.s., Novara (IT)

(72) Inventors: Umberto Dianzani, Turin (IT); Casimiro Luca Gigliotti, Novara (IT); Elena Boggio, Mezzomerico (IT); Nausicaa Clemente, Cossato (IT); Annalisa Chiocchetti, Turin (IT); Francesco Trotta, Asti (IT); Roberta Cavalli, Alessandria (IT); Chiara Dianzani, Turin (IT)

(73) Assignee: NOVAICOS IMMUNOTHERAPEUTICS S.R.L., Colleretto Giacosa (IT)

(*) Notice: Subject to any disclaimer, the term of this patent is extended or adjusted under 35 U.S.C. 154(b) by 1090 days.

(21) Appl. No.: 16/963,185

(22) PCT Filed: Jan. 9, 2019

(86) PCT No.: PCT/IB2019/050154
§ 371 (c)(1),
(2) Date: Jul. 17, 2020

(87) PCT Pub. No.: WO2019/142070
PCT Pub. Date: Jul. 25, 2019

(65) Prior Publication Data
US 2021/0128684 A1    May 6, 2021

(30) Foreign Application Priority Data

Jan. 18, 2018 (IT) .................. 102018000001315

(51) Int. Cl.
*A61K 38/17* (2006.01)
*A61K 47/69* (2017.01)

(52) U.S. Cl.
CPC ...... *A61K 38/1774* (2013.01); *A61K 47/6939* (2017.08); *C07K 2319/30* (2013.01)

(58) Field of Classification Search
CPC ........ A61K 47/50; A61K 47/51; A61K 47/52; A61K 47/54; A61K 47/543; A61K 47/544; A61K 47/549; A61K 47/56; A61K 47/58; A61K 47/593; A61K 47/595; A61K 47/60; A61K 47/61; A61K 47/68; A61K 47/69; A61K 47/6905; A61K 47/6907; A61K 47/6911; A61K 47/6913; A61K 47/6915; A61K 47/6917; A61K 47/6921; A61K 47/6923; A61K 47/6925; A61K 47/6927; A61K 47/6929; A61K 47/6931; A61K 47/6937; A61K 47/6939; A61K 47/6951; A61K 47/6957; A61K 9/14; A61K 9/16; A61K 9/50; A61K 9/51; C07K 2318/20; A61P 35/00; A61P 35/02; A61P 35/04

See application file for complete search history.

(56) References Cited

U.S. PATENT DOCUMENTS

| 2003/0158102 | A1* | 8/2003 | Chen ................ C07K 14/70532 514/6.9 |
| 2012/0114595 | A1* | 5/2012 | Kajihara .............. A61K 38/177 424/85.1 |

FOREIGN PATENT DOCUMENTS

WO    2016/189428 A1    12/2016

OTHER PUBLICATIONS

Bakkour and Sha, Journal of Immunological Methods, 2008, vol. 332, pp. 151-161). (Year: 2008).*
Minelli et al (British Journal of Pharmacology, 2012, vol. 166, pp. 587-601) (Year: 2012).*
Greish (Journal of Drug Targeting, 2007, vol. 15, pp. 457-464) (Year: 2007).*
Wang et al (Journal of Experimental Medicine, 2002, vol. 195, pp. 1033-1041) (Year: 2002).*
Dianzani, C., et al., "B7h Triggering Inhibits the Migration of Tumor Cell Lines," The Journal of Immunology, 2014, 192:4921-4931.
Dianzani, C., et al., "B7h Triggering Inhibits Umbilical Vascular Endothelial Cell Adhesiveness to Tumor Cell Lines and Polymorphonuclear Cells," The Journal of Immunology, 2010, 185:3970-3979.
Zamarin, D., et al., "Intratumoral Modulation of the Inducible Co-Stimulator ICOS by Recombinant Oncolytic Virus Promotes Systemic Anti-Tumor Immunity," Nature Communications, Feb. 2018, pp. 1-14.
Ara, G., et al., "Potent Activity of Soluble B7RP-1-FC in Therapy of Murine Tumors in Syngeneic Hosts," Int. J. Cancer: 103, 501-5807 (2003).
Fu, T., et al., "The ICOS/ICOSL Pathway is Required for Optimal Antitumor Responses Mediated by Anti-CTLA-4 Therapy," Cancer Research; 71(16); 5445-54.

* cited by examiner

Primary Examiner — Karen A. Canella

(74) Attorney, Agent, or Firm — Nixon & Vanderhye, PC

(57) ABSTRACT

Novel anti-tumor agents comprising at least one ligand of the B7h receptor, wherein the ligand of receptor B7h is loaded in a biocompatible micro- or nano-carrier and is able of binding to receptor B7h and triggering receptor B7h activity.

21 Claims, 7 Drawing Sheets
Specification includes a Sequence Listing.

ANTI-TUMOR THERAPEUTIC AGENTS BASED ON B7h RECEPTOR LIGANDS

CROSS-REFERENCE TO RELATED APPLICATIONS

This application is the U.S. national phase of International Application No. PCT/IB2019/050154 filed Jan. 9, 2019 which designated the U.S. and claims priority to IT Patent Application No. 102018000001315 filed Jan. 18, 2018, the entire contents of each of which are hereby incorporated by reference.

REFERENCE TO SEQUENCE LISTING SUBMITTED ELECTRONICALLY

The content of the electronically submitted sequence listing (Name: (4636_0466_ST25.txt; Size: 31.9 kilobytes; and Date of Creation: Jul. 17, 2020) filed with the application is incorporated herein by reference in its entirety.

FIELD OF THE INVENTION

The disclosure concerns novel anti-tumor therapeutic agents comprising at least one ligand of the receptor B7h.

BACKGROUND OF THE INVENTION

ICOS is a T cell costimulatory molecule described by the present inventors as H4[1,2]. Later on, Hutloff cloned ICOS as a molecule belonging to the CD28 family and it was shown that ICOS and H4 are the same molecule[3,4]. A distinctive feature of ICOS is its selective expression in activated T cells, but it has been recently detected also in dendritic cells (DC)[5]. The ICOS receptor is ICOSL (or B7h), expressed by several cell types, such as DC, macrophages, B cells, endothelial cells (EC), epithelial cells, and fibroblasts[6]. The ICOS/B7h interaction regulates T cell activation in lymphoid organs and controls T cell function at inflammation sites. It supports differentiation of Treg, TH17, and follicular T helper cells and development of germinal centers and its deficiency causes common variable immunodeficiency[7-11].

Other names for B7h are Inducible T-Cell Costimulator Ligand (ICOSL or ICOS-L), B7-Related Protein 1 (B7RP-1 or B7RP1) B7 Homolog 2 (B7-H2), B7-Like Protein G150, GL50, KIAA0653, LICOS, CD275. The B7h:ICOS interaction triggers bidirectional signals modulating the response of the B7h-expressing cells. In mouse DC, this B7h-mediated "reverse signalling" increases IL-6 secretion[12]. To assess the effects of B7h triggering in vitro and in vivo, the present inventors produced a bivalent soluble form of ICOS composed by the Fc portion of IgG1 and two molecules of the extracellular portions of ICOS (ICOS-Fc). Since ICOS-Fc is bivalent, it crosslinks B7h and exerts an agonist effect triggering B7h signaling in the B7h-expressing cells. In human cells, the following effects of B7h triggering by ICOS-Fc were shown. i) In EC and tumor cell lines, it inhibits adhesiveness and migration in vitro[13,14]. ii) In tumor cell lines, it inhibits development of experimental lung metastases in vivo[14]. iii) In DC, it modulates cytokine secretion by increasing secretion of IL-23 (supporting TH17 differentiation involved in the anti-tumor response), promotes antigen cross-presentation, and inhibits adhesiveness and migration in vitro[15]. iv) In osteoclasts (OC), it inhibits differentiation from monocytes and bone resorption ability in vitro, and development of osteoporosis in mice in vivo[16]. v) B7h triggering induces dephosphorylation of ERK and p38 in EC, dephosphorylation of FAK in tumor cells, and down-modulation of β-Pix in DC and tumor cells[13-15].

SUMMARY OF THE INVENTION

The object of this disclosure is to provide novel anti-tumor therapeutic agents comprising at least one ligand of the receptor B7h, wherein the ligand of receptor B7h is able to bind specifically to receptor B7h and to trigger the receptor B7h activity.

According to the invention, the above object is achieved thanks to the subject matter recalled specifically in the ensuing claims, which are understood as forming an integral part of this disclosure.

The present invention provides a ligand of receptor B7h for use in the treatment of a subject suffering from a tumor, wherein the ligand of receptor B7h is loaded into or onto a biocompatible micro- or nano-carrier, and the ligand of receptor B7h is able of binding the receptor B7h and triggering the receptor B7h activity.

BRIEF DESCRIPTION OF THE DRAWINGS

The invention will now be described in detail, purely by way of illustrative and non-limiting example, with reference to the attached figures, wherein.

DETAILED DESCRIPTION OF THE INVENTION

Figure 1:
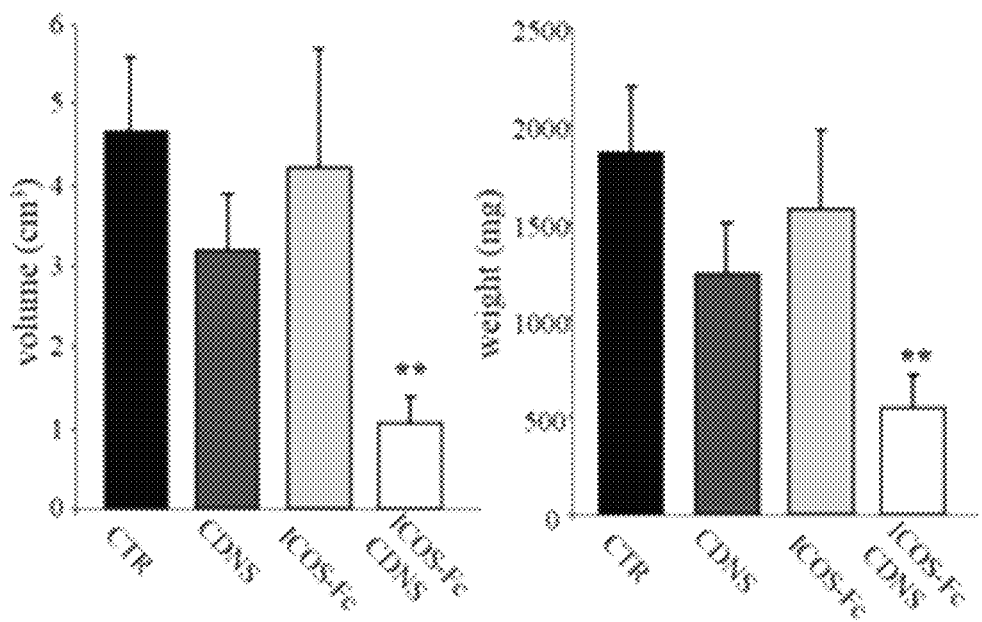
FIG. 1: Effect of different forms of ICOS-Fc on the growth of B16-F10 tumors in C57BL/6 mice. Mice with palpable subcutaneous B16 tumors were treated every 4 days with PBS, CDNS (nanoparticles) alone, ICOS-Fc or CDNS loaded with ICOS-Fc. The tumor growth was evaluated 16 days after the first treatment. Each treatment involved 5 mice/experiment. **$p<0.05$ vs each other condition.

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

The instant disclosure concerns novel anti-tumor therapeutic agents comprising at least one ligand of receptor B7h having the ability of triggering the receptor B7h activity.

According to one embodiment, the present invention provides for a ligand of receptor B7h for use in the treatment of a subject suffering from a tumor, wherein the ligand of receptor B7h is loaded into or onto a biocompatible micro- or nano-carrier, and the ligand of B7h receptor is able of binding the receptor B7h and triggering the receptor B7h activity, and optionally inhibiting osteopontin activity.

In a preferred embodiment, the ligand of receptor B7h is selected from:
  a) a human ICOS protein having an amino acid sequence as set forth in SEQ ID No.: 1 or portions thereof;
  b) a human ICOS extracellular domain having an amino acid sequence as set forth in SEQ ID No.: 2 or portions thereof; and
  c) a homologue of any one of proteins a) and b) having at least 80%, preferably at least 90%, more preferably at least 95%, still more preferably at least 98%, sequence identity to the amino acid sequences as set forth in SEQ ID No.: 1, 2 or portions thereof.

In a still further preferred embodiment, the ligand of B7h receptor comprises an amino acid sequence as set forth in SEQ ID No.: 3.

In one embodiment of the present invention, the ligand of receptor B7h loaded into or onto a biocompatible micro- or nano-carrier is to be administered by injection, infusion.

As used herein, the expression "ligand of receptor B7h" comprises the human wild type ligand ICOS having an amino acid sequence as set forth in SEQ ID No.: 1, as well as portions of the same (for example having an amino acid sequence as set forth in SEQ ID No.: 2) provided that such portions have the ability of binding receptor B7h, triggering its activity and optionally inhibiting osteopontin activity.

Other ligands of receptor B7h useful within the present invention comprise monoclonal antibodies able to bind specifically receptor B7h (i.e. with high affinity), provided that such monoclonal antibodies have agonistic activity towards B7h receptor, i.e. they are able to trigger the receptor B7h activity, and optionally have antagonistic activity towards osteopontin, i.e. they are able to inhibit the osteopontin activity.

The expression "homologue of human ICOS or portions thereof" means proteins having at least 80%, preferably at least 90%, more preferably at least 95%, still more preferably 98%, identity with any one of the SEQ ID NO.: 1 and 2 or portions thereof, provided that such homologues have the ability of binding receptor B7h and triggering its activity, and optionally inhibiting the osteopontin activity.

It is common general knowledge that the ability of triggering a receptor activity implies the ability to cross-link the receptor of interest expressed on the cell surface as indicated e.g. in Seed B. "Making agonists of antagonists", Chem Biol. 1994 November; 1(3):125-9, and A, Schlessinger J. "Signal transduction by receptors with tyrosine kinase activity", Cell. 1990 Apr. 20; 61(2):203-12. From such common general knowledge it derives that ligand of receptor B7h needs to be in at least a dimeric form for exerting the anti-tumor effect. Examples of ligands in at least a dimeric form able to trigger receptor B7h activity are represented i.a. by bivalent o multivalent ICOS-Fc constructs, anti-B7h receptor antibodies, organic/inorganic, natural/synthetic scaffolds comprising at least two ICOS molecules attached thereto and ICOS multimers obtained by chemical or genetic crosslinking of multiple ICOS molecules. Multimerization may be achieved by metal ion- or small molecule-based assembly, protein (peptide) interaction-based assembly, covalent protein assembly, genetic fusion of functional proteins to protein building blocks. Multimerization may be achieved by use of dendrimers, dendrons, dendronized polymers, hyperbranched polymers, and polymer brushes. The scaffolds may include organic polymers (such as those derived from sucrose, squalene or solanesol), and organic or inorganic solid nano/microparticles exposing multiple ICOS molecules on their surface.

In one embodiment, the present invention provides for the ligand of receptor B7h being fused or conjugated to a stabilizing molecule.

With respect to the stabilizing molecules that can be conjugated with the receptor B7h ligand, such molecules are widely known in the art and do not necessitate a detailed description herein. As examples of stabilizing molecules, one can cite human Fc antibody domain, polyethylene glycols (PEGs) or derivatives thereof, poly-L-lysine citramide (via a lysine or an ethylcarbamate spacer), styrenemaleic acid anhydride and poly-hydroxypropylmetacrylamide.

PEG derivatives able to link amino groups present on the receptor B7h ligands are i.a. epoxide PEG, aldehyde PEG, nitrophenyl carbonate PEG and succinimidyl ester PEG; PEG derivatives able to link thiol groups present on the B7h receptor ligands are i.a. orthopyridyl disulfide PEGs; PEG derivatives able to link hydroxyl groups present on the B7h receptor ligands are i.a. PEG-COOH activated with N-hydroxysuccinimide or hydroxybenzotriazole. Other PEG derivatives are represented by PEG-polyacetal with pH-dependent hydrolysis, and PEG-dextrin (polymer-masking-unmasking-protein therapy, PUMPT).

In order to increase the delivery of the B7h receptor ligand to the site of treatment, namely the tumor, the receptor B7h ligand may also be hyperglycosylated or conjugated to mannose residues.

Hyperglycosylation may be performed by either in situ chemical reactions or site-directed mutagenesis resulting in either N-linked or O-linked protein glycosylation. In N-linked glycosylation, the saccharide chain is attached to asparagine of tripeptide sequence Asn-X-Ser/Thr, where X represents an amino acid other than proline. Polysialic acid (PSA) is often used for hyperglycosylation. Large-molecular-weight PSAs are suitable for the delivery of low-molecular-weight drugs and peptides, while lower molecular weight PSAs could be used for large proteins as well as particulate drug-delivery systems.

The conjugation to mannose residues exploits binding of the conjugate to mannose receptors, which are reported to be expressed on Kupffer cells, macrophages, alveolar, monocyte-derived dendritic cells and subsets of vascular and lymphatic endothelial cells. Mannosylated proteins can be recognized by mannose-specific lectins, namely, mannose receptors and MBPs.

With respect to the biocompatible carrier (which may have different degrees of biodegradability), the carrier is selected from particles, capsules, vesicles, bubbles, each of them having dimensions in the order of micron or nanometers. Other suitable carriers are represented by nanoemulsions, nanosuspensions, nanohydrogels, micelles, dendrimers, quantum dots, liposomes or carbon derivatives (e.g. carbon nanotubes). The micro-, nano-particles can be made of polymers, metals (e.g. gold), silica or a synthetic polymer core with a lipoid shell. The metal particles may also be magnetic. All these carriers are widely known in the pharmaceutical field for the delivery of drugs and do not necessitate a detailed description herein. The antitumor activity of the receptor B7h ligand/carrier system is not related to a specific type of carrier, but the association of receptor B7h ligand to a nano/microcarrier create a micro-, nano-platform formulation wherein the two components work together. The loading of the B7h receptor ligand into or onto a micro/nanocarrier is crucial for its therapeutic effectiveness and for clinical translation. The carrier and the ligand of receptor B7h equally contribute to the antitumor activity and their synergistic effect is mandatory for an effective anticancer therapy. Additionally, the B7h receptor ligand/carrier system is important to magnify the antitumor activity as described below. The incorporation of the receptor B7h ligand within a carrier create a reservoir of the active molecule and minimize its systemic exposure, allowing accumulation and release to tumor tissues and avoiding non specific delivery. Indeed, the incorporation of the receptor B7h ligand in micro/nanocarrier allows the development of site-specific targeted systems for delivering to cancer cells, exploiting passive and active targeting strategies.

In a preferred embodiment, the carrier is represented by micro- or nano-particles made of cyclodextrin polymer, poly(lactide-co-glycolic acid) (PLGA), polycaprolactone, (PCL), polylactic acid (PLA), poly(glycolide), chitosan, alginate, starch, alginate, collagen, albumin, silica, metal. Preferably the carrier is represented by micro- or nano-particles made of cyclodextrin polymer or poly(lactide-co-glycolic acid).

In a further embodiment, the present invention concerns a pharmaceutical composition comprising at least one ligand of receptor B7h loaded into or onto a biocompatible micro- or nano-carrier and a pharmaceutical acceptable vehicle for use in the treatment of a tumor.

In a preferred embodiment, the at least one ligand of receptor B7h contained in the pharmaceutical composition is selected from:
  a) a human ICOS protein having an amino acid sequence as set forth in SEQ ID No.: 1 or portions thereof;
  b) a human ICOS extracellular domain having an amino acid sequence as set forth in SEQ ID No.: 2 or portions thereof; and
  c) a homologue of any one of proteins a) and b) having at least 80%, preferably at least 90%, more preferably at least 95%, still more preferably at least 98%, sequence identity to the amino acid sequences set forth in SEQ ID No.: 1, 2 or portions thereof.

In a still preferred embodiment, the at least one ligand of receptor B7h contained in the pharmaceutical composition comprises an amino acid sequence as set forth in SEQ ID No.: 3.

In a preferred embodiment, the at least one ligand of receptor B7h contained in the pharmaceutical composition is fused or conjugated to a stabilizing molecule.

The present disclosure also concerns use of receptor B7h as target for the screening of pharmaceutical active agents useful in the treatment of a tumor, wherein the pharmaceutically active agents bind to receptor B7h, trigger receptor B7h activity and inhibit osteopontin activity.

Previous work in vitro showed that B7h triggering by ICOS-Fc inhibits migration and adhesion of DC, EC and several tumor cell lines. Moreover, in vivo studies showed that ICOS-Fc inhibits the metastatization into the lungs of B7h-positive tumor cells injected in the tail vein. By injecting human B7h-positive neoplastic cells in the tail vein of mice and treating these mice with both mouse and mouse ICOS-Fc (which are species-specific), the present inventors showed that the ICOS-Fc-mediated inhibition of in vivo metastatization involves effects on both the tumor cells and the host cells. In vivo treatment with ICOS-Fc inhibited development of experimental lung metastases upon injection of B16 melanoma cells in the tail vein of syngeneic mice. Moreover, using the xenograft model of human CF-PAC1 cell line injected in the tail vein of NOD-SCID-IL2Rγnull (NSG) mice, the present inventors found that optimal inhibition of metastatization requires contemporary treatment with both the human and the mouse ICOS-Fc. These data indicate that ICOS-Fc exerts its inhibitory effect on metastatic dissemination by acting on both the human tumor cells and the mouse environment[14].

The tumor growth actually involves several distinct processes, such as neoplastic cell proliferation and apoptosis, tissue invasion, adhesion and migration, angiogenesis, intra- and extra-vasation. Therefore, anti-metastatic drugs acting on neoplastic cell adhesion, migration, intra- and extra-vasation (so called "migrastatic" agents) are not effective on the tumor growth, and the potential clinical relevance of "migrastatic" agents is now heavily questioned[17,18]. In fact, the previous experiments of the inventors did not detect any effect of ICOS-Fc on the growth of established primary tumors either in vivo[13,14] or in vitro. These negative results have been obtained in vivo testing several doses and delivery routes of ICOS-Fc (intravenous, intraperitoneal, and peritumoral injection) and several experimental models of tumor expressing B7h (transplantable B16 melanoma and PC3 prostate carcinoma and Balb/neuT spontaneous mammary carcinoma). In vitro experiments, indeed, did not detect any effect of ICOS-Fc on the proliferation and apoptosis of several tumor cells lines expressing B7h[14]. Moreover, ICOS-Fc did not show any effect on vascular endothelial cell proliferation and angiogenesis assays in vitro[14]. In conclusion, the only anti-tumor effect of ICOS-Fc detected by the previous studies was the anti-metastatic one, whereas no effects were detected on the tumor growth in vivo, and tumor cell proliferation and apoptosis, and angiogenesis in vitro.

The present inventors then tested the anti-tumor activity of ICOS-Fc encapsuled in biocompatible nanoparticles.

Using the B16 melanoma model of transplantable tumor, the inventors found unexpectedly that ICOS-Fc encapsulated in cyclodextrin polymer nanosponges (CDNS) display a potent anti-tumor activity decreasing the growth of established tumor masses and decreasing its vascularization. These effects were detectable also in ICOS-deficient mice, which shows that they were not ascribable only to an antagonistic effect of ICOS-Fc on the interaction between B7h and the endogenous ICOS. The effect was not dependent on the nanoparticle type and the tumor type since a similar anti-tumor effect was detected using human ICOS-Fc loaded in poly(lactide-co-glycolic acid) (PLGA) nanoparticles and in a xenogeneic model of glioblastoma.

Another aspect of the B7h involvement in the antitumor response is that the present inventors found that B7h binds also osteopontin (OPN), that can act either as a protein of the extracellular matrix and a soluble cytokine. OPN is secreted by several cell types including macrophages, DC, osteoblasts, and T cells. It mediates several functions such as bone remodeling, macrophage response, cell migration and adhesion, inflammation, and support of TH1 and TH17 cell differentiation. In the tumor biology, OPN produced by tumor cells and the tumor microenvironment plays a key role in promoting tumor growth, migration, metastatic dissemination, and neoangiogenesis. OPN interacts with several receptors, such as integrins and CD44, and it is cleaved by thrombin in a N-terminal (OPN-N) and a C-terminal (OPN-C) portion, which bind to different receptors and exert different functions. A RGD domain binding to several integrins is located in OPN-N nearby to two other binding sites for the $\alpha_4\beta_1$ integrin, which are exposed upon thrombin cleavage; a CD44 binding site is located in OPN-C[19]. The present inventors found unexpectedly that B7h expression is required for the OPN-induced migratory response of tumor cell lines and EC and this effect is inhibited by ICOS-Fc. Then, it was found that OPN directly binds to B7h using a binding site of B7h different from that bound by ICOS. These data depict a scenario in which B7h triggering by ICOS inhibits cell migration induced by several chemoattrancts whereas its triggering by OPN induces cell migration, with a dominant effect exerted by ICOS. Therefore, without being bound to any specific theory, the present inventors have reasons to believe that ICOS-Fc exerts its anti-tumor effects also by inhibiting the OPN effects promoting tumor growth, migration, metastatic dissemination, and neoangiogenesis.

With respect to the carrier for delivery of the B7h receptor ligand for its use in the treatment of a tumor, the present inventors verified that the nature of the carrier has not any effect on the ability of the B7h receptor ligand of exerting its anti-tumor activity.

The micro-, nano-particles can be made of cyclodextrin (CD) polymer nanosponges (CDNS), poly(lactide-co-glycolic acid) (PLGA), polycaprolactones (PCL), polylactic acid (PLA), poly(glycolide), chitosan, alginate, starch, dextran, collagen, albumin, silica, metal (e.g. gold). Liposomes may also be surface modified with PEG in order to interfere with recognition and uptake by reticulo endothelial system and to extend circulation time. Moreover, in situ thermosensitive hydrogels undergo sol-gel phase transition in response to changes in temperature.

CD are cyclic α-1,4-glucans comprising from six to >100 glucose units. They are natural products resulting from intramolecular transglycosylation reactions of starch degraded by CD glucanotransferase. The enzymatic product is generally a mixture of α, β, γ-CD comprising six, seven, and eight glucose units respectively. They play an important role in supramolecular chemistry due to their ability for molecular encapsulation with a wide range of guest molecules and are of high interest in the pharmaceutical field, biomedical science and biotechnology. They present a torus-shaped ring structure with an interior hydrophobic cavity and a hydrophilic exterior site. NS can form nanoporous insoluble nanoparticles (NP) due to the presence of CD cavities and the nanochannels of the cross-linked network with a crystalline or amorphous structure, spherical shaped, and with swelling properties[20-24].

Cyclodextrin-nanosponges (CDNS) can form inclusion complexes able to host a wide range of hydrophobic molecules. In aqueous solution, the hydrophobic CD cavity is occupied by water molecules bounded by "weak forces" (energetically unfavoured). Owing to the size of the internal cavity, one or two hydrophobic guest molecule(s) may be entrapped by one, two, or even three CD. CDNS can form porous insoluble NP, either crystalline or amorphous, with a spherical shape. The polarity and dimension of the polymer mesh can be easily tuned by varying the type and degree of cross-linking. CDNS can incorporate different types of lipophilic or hydrophilic molecules, and they can be functionalized for site-specific targeting by conjugating various ligands on their surface. They are safe and biodegradable, display negligible toxicity on cell cultures, and are well-tolerated upon injection in mice. Release of the entrapped molecules can be modulated by adjusting the NS structure to achieve to improve the aqueous solubility of poorly water-soluble molecules, protect degradable substances, and obtain sustained release.

Poly(lactic-co-glycolic acid) (PLGA) NPs are the best characterized NPs that increase potency and bioavailability of several drugs and their use has been approved by the Food and Drug Administration (FDA) for several therapeutic applications. The modulation of the polymer lactide-glycolide ratio, molecular weight and crystal profile allows to protract the degradation rate and subsequent release of the entrapped molecules from several days up to one year.

Figure 4:
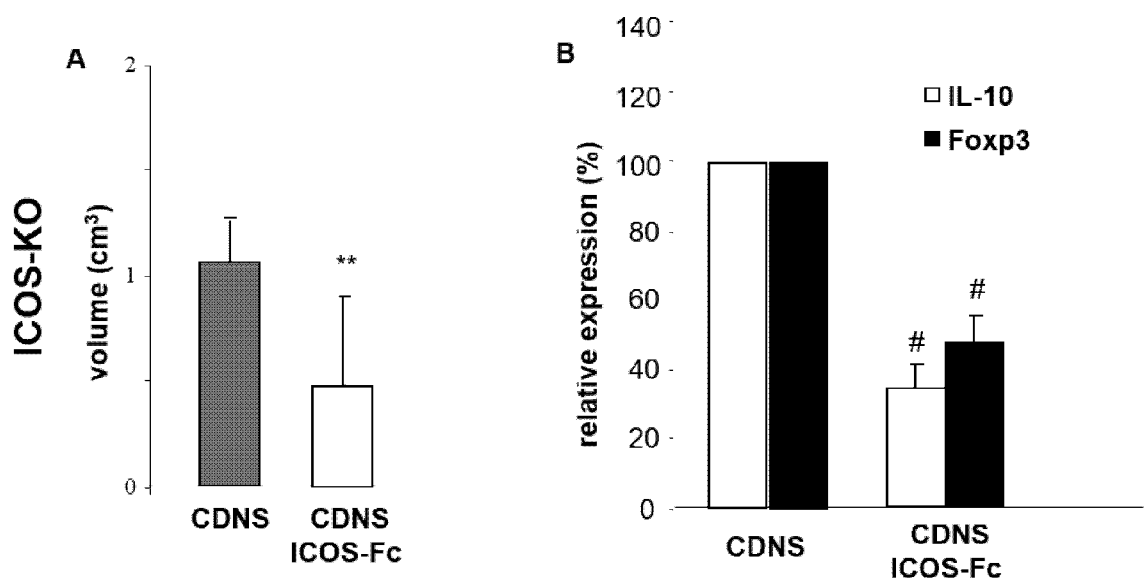
FIG. 4: Effect of different forms of ICOS-Fc on the growth of B16-F10 tumors in ICOS-deficient C57BL/6 mice. Mice with palpable subcutaneous B16 tumors were treated every 4 days with CDNS alone or CDNS loaded with ICOS-Fc. (A) Tumor growth was evaluated 8 days after the first treatment; each treatment involved 8 mice. **$p<0.05$. (B) Expression of IL-10 and Foxp3 in tumor infiltrating lymphocytes analyzed by real time PCR analysis; the data are normalized for the expression in the CDNS control. #$p<0.05$ from the respective value in mice treated with CDNS.
Figure 9:
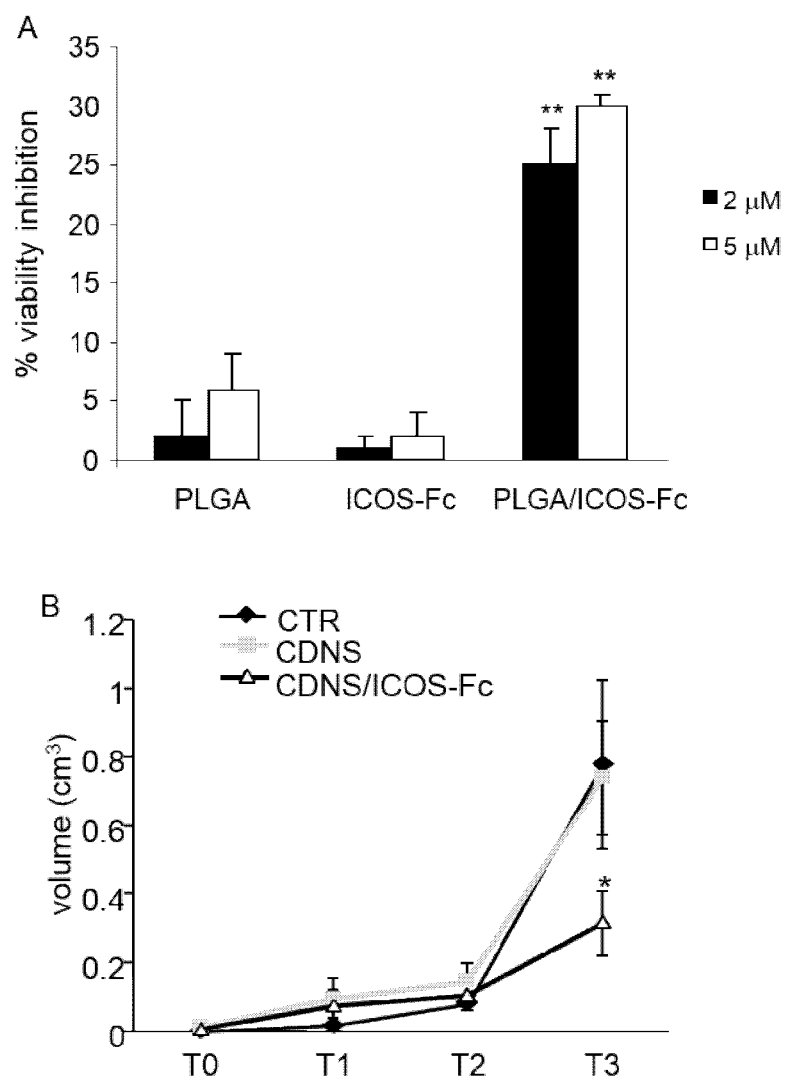
FIG. 9: Effect of PLGA/ICOS-Fc on the survival of B16-F10 cells in vitro and the growth of B16-F10 tumors in C57BL/6 mice. (A) Cell viability of B16-F10 cells was assessed by MTT upon culture in the presence and absence of titrated amounts (0.5-5 µg/ml) of free ICOS-Fc, or empty PLGA NP or PLGA/ICOS-Fc NP. Results are shown as inhibition % of the viability detected in cells cultured in the absence of those reagents. (B) Mice with palpable subcutaneous B16 tumors were treated every 4 days with PBS, PLGA (nanoparticles) alone, PLGA/ICOS-Fc. The tumor growth was evaluated 16 days after the first treatment. Each treatment involved 5 mice/experiment. *or** $p<0.05$ vs each other condition.

In the instant description, the present inventor show that ICOS-Fc significantly inhibits the growth of established primary tumors only when it is encapsulated in biocompatible nanoparticles, whereas the free ICOS-Fc has no effect (FIG. 1). This has been detected in both a strongly immunogenic peripheral tumor (melanoma) and a weakly immunogenic CNS tumor (glioblastoma), using either CDNS or PLGA nanoparticles as the drug carriers, and using either a mouse tumor model (melanoma) (FIG. 1) or a human/mouse tumor xenograft model (glioblastoma) (FIG. 9). Moreover, ICOS-Fc was effective not only in immunocompetent mice (melanoma) (FIG. 1), but also in athymic mice (glioblastoma) (FIG. 9) and ICOS-KO mice (melanoma) (FIG. 4). These data show that the ICOS-Fc effect was not ascribable to blocking the interaction between B7h and the endogenous ICOS expressed on T cells (or other cell types). This blocking, using an anti-ICOS mAb, has been shown to inhibit the development of Treg cells suppressing the antitumor immune response.

Without wishing to be bound to any theory, the present inventors have reasons to believe that the loading of ICOS-Fc in the carrier (nanoparticles) for exerting its anti-tumor activity may be ascribed to the carrier ability to carry ICOS-Fc into the tumor mass possibly through the Enhanced Permeability and Retention (EPR) effect. The same effect may be exerted by various types of carriers acting either through EPR or other mechanisms to increase drug delivery into the tumor, such as carriers conjugated to biomolecules increasing targeting into the tumor. Moreover, the same effect of ICOS-Fc may be exerted by other molecules capable to trigger B7h, such as monoclonal antibodies.

Figure 2:
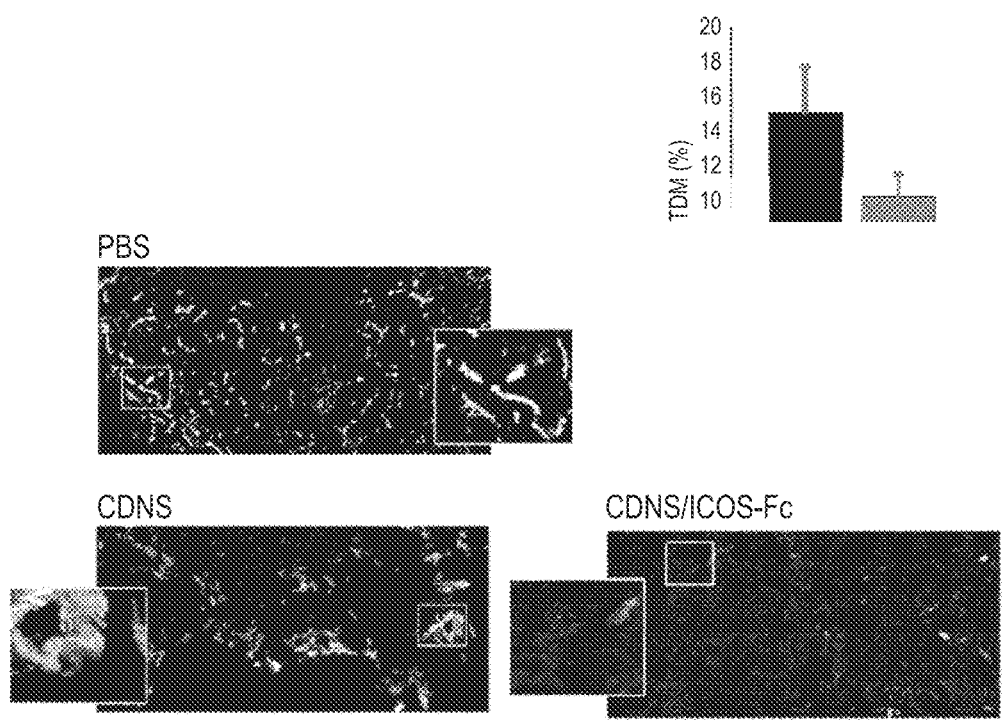
FIG. 2: Effect of CDNS/ICOS-Fc on tumor angiogenesis in vivo. Immunofluorescence staining for anti-CD31 of tumors tissue sections from mice treated with PBS, CDNS alone or CDNS loaded with ICOS-Fc. The slides were stained with either Ab rabbit α-mouse CD31 plus a secondary antibody α-rabbit conjugated with Alexa Fluor® 488. Representative images of 3 independent experiments are shown. The bar graph shows the cumulative results of these experiments as tumor microvessel density (TDM). **$p<0.05$ vs each other condition.
Figure 5:
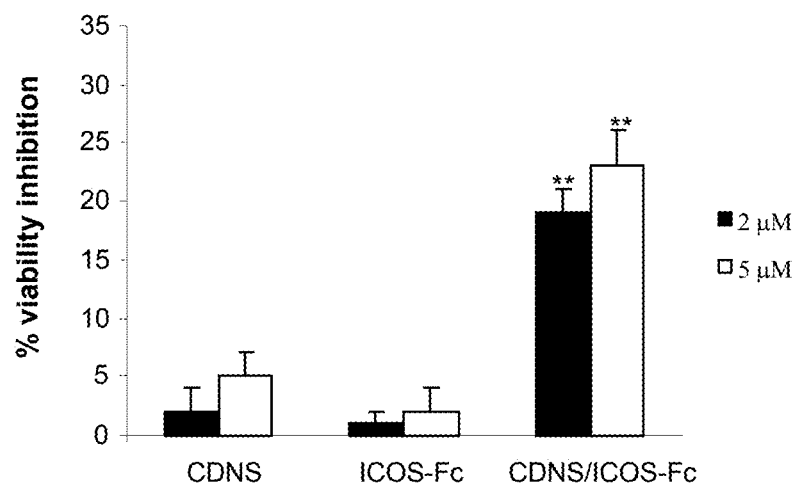
FIG. 5 Effect of different forms of ICOS-Fc on the viability of B16-F10 cells in vitro. Cell viability of B16-F10 cells was assessed by MTT upon culture in the presence and absence of titrated amounts (0.5-5 µg/ml) of free ICOS-Fc, or empty CDNS or CDNS/ICOS-Fc. Results are shown as inhibition % of the viability detected in cells cultured in the absence of those reagents.

The antitumor activity of B7h triggering may be partly ascribed to the ICOS-Fc effect on tumor angiogenesis, as suggested by the antiangiogenic activity of ICOS-Fc in vitro (FIG. 8) and in vivo (FIG. 2). This finding is novel since previous data did not detect any antiangiogenic effect exerted by ICOS-Fc[14]. Moreover, the effect of the human ICOS-Fc in the glioblastoma xenograft model shows that ICOS-Fc exerts also a direct effect on the tumor cells, since the human ICOS-Fc does not interact with the mouse B7h expressed by the host cells. In support of a direct effect of ICOS-Fc encapsulated in NP on the tumor cell viability, the inventors show that high doses of ICOS-Fc encapsulated in CDNS exert a cytotoxic effect on B16-F10 cells in vitro, whereas empty CDNS and free ICOS-Fc had no effect (FIG. 5). One possibility is that the difference may be due to the NP ability to increase the ICOS-Fc cell internalization, which would increase the ICOS-Fc interaction with the intracellular receptor B7h.

Figure 6:
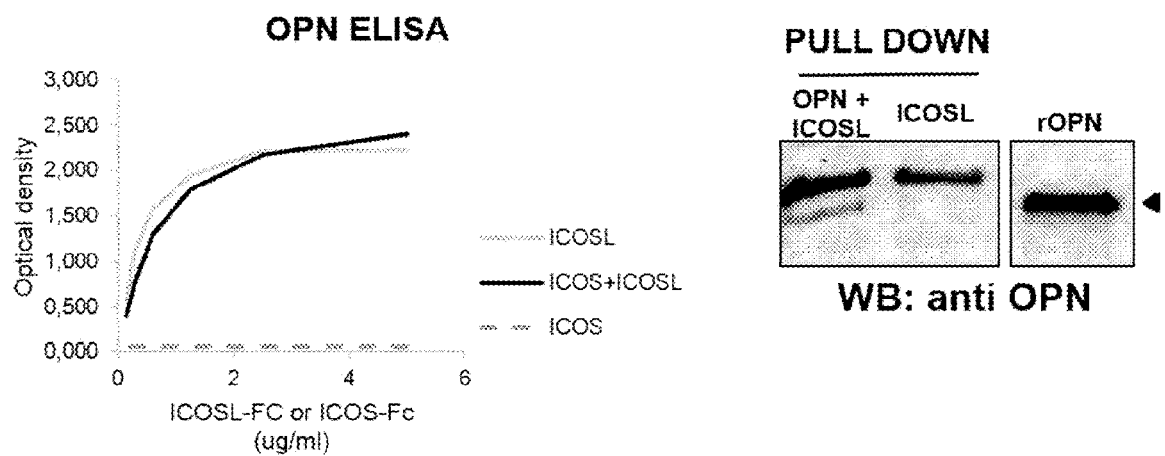
FIG. 6. Results of two approaches detecting the interaction of OPN with B7h. (Left) It shows the interaction of titrated amounts of soluble B7h-Fc (grey line) with a fixed amount of osteopontin (OPN) coated on the ELISA plate. The black line shows the same experiment in the presence of 5 µg/ml of soluble ICOS-Fc to evaluate the competition between ICOS and OPN for B7h binding. The dashed line shows the lack of binding of titrated amounts of soluble ICOS-Fc to the OPN-coated plates. (Right) The Western blot shows a pull-down assay in which B7h-Fc was used as a sepharose-bound bait protein incubated (first lane) or not (second lane) with OPN. The third lane was the OPN positive control. The membrane was blotted with an anti-OPN polyclonal antibody.
Figure 7:
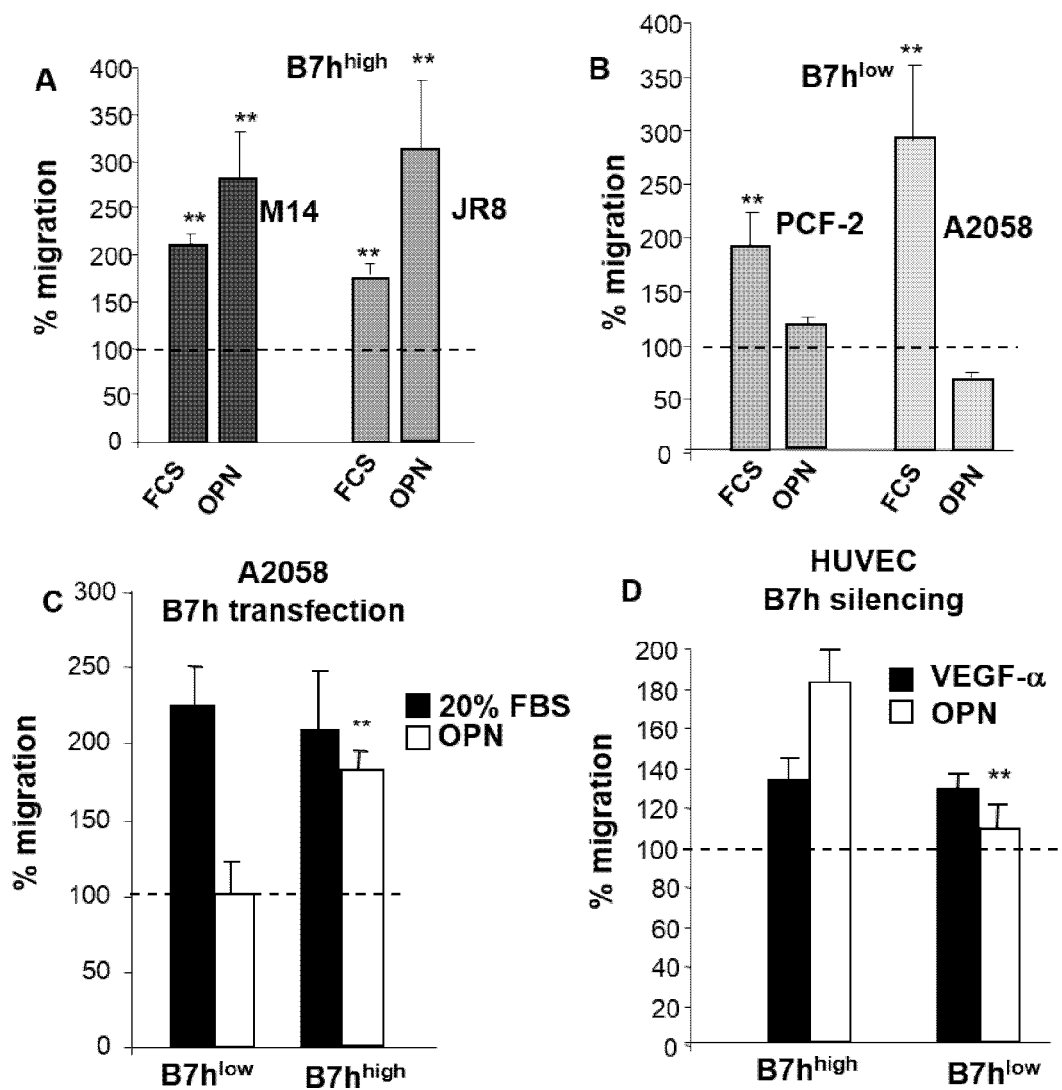
FIG. 7. Role of B7h in OPN function. (A-B) Cell migration induced in tumor cell lines expressing high (A) and low (B) levels of B7h by OPN or FCS;  significantly different from untreated cells. (C) The migratory response to OPN is restored in B7h-transfected (B7h$^{high}$) A2058 cell;  significantly different from untransfected cells (B7h$^{low}$). (D) The migratory response to OPN is suppressed in B7h-silenced (B7h$^{low}$) HUVEC; ** significantly different from unsilenced cells (B7h$^{high}$) The dotted horizontal lines correspond to basal migration of untreated cells, set al 100%.
Figure 8:
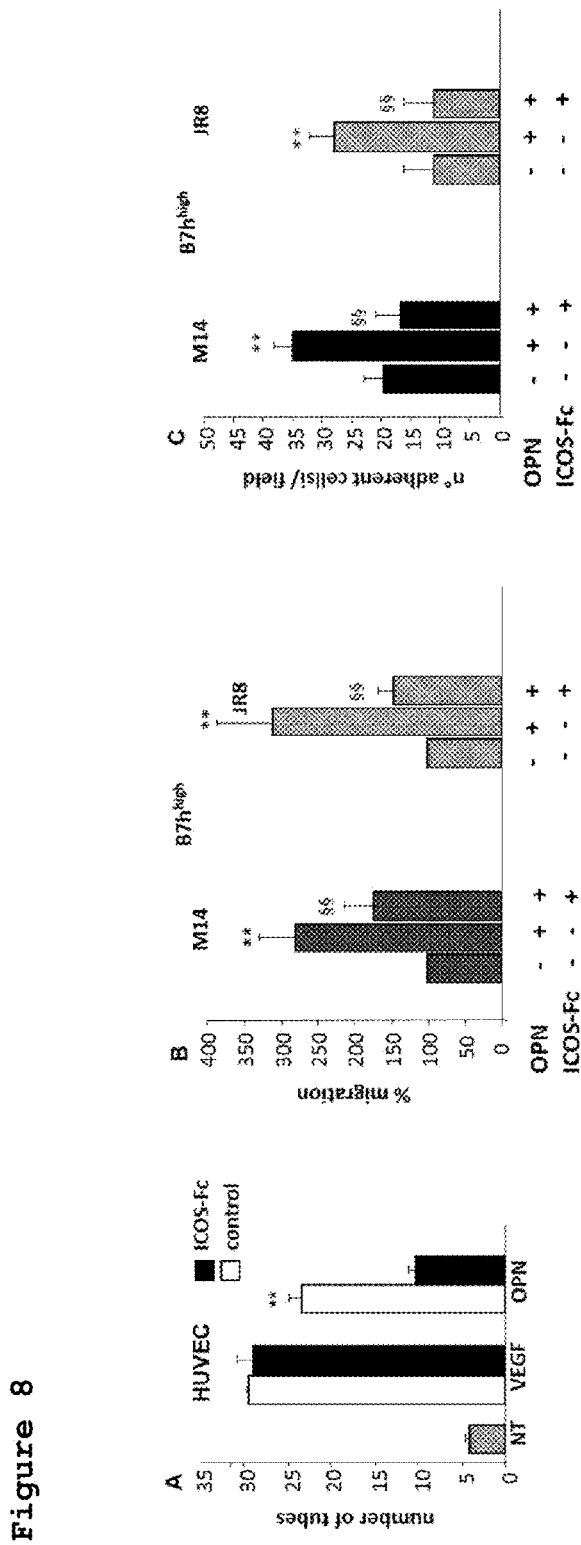
FIG. 8. Effect of ICOS-Fc in OPN-induced tubulogenesis and tumor cell migration and adhesion. (A) Effect of ICOS-Fc on HUVEC tubulogenesis induced by either OPN or VEGF; NT: basal tube formation without OPN and VEGF.  significantly different from the corresponding cells treated with ICOS-Fc. (B-C) Effect of ICOS-Fc on migration (B) and adhesion (C) to HUVEC of two human melanoma cell lines expressing high levels of B7h (i.e. M14 and JR8).  $p<0.05$ versus untreated cells; §§ $p<0.05$ vs OPN-treated cells.

A key point is that it has been shown for the first time that B7h also binds to OPN (FIG. 6), which is a key molecule involved in the tumor growth, migration and metastatization, and the B7h/OPN interaction is involved in these OPN activities (FIG. 7). The B7h/OPN interaction involves a different binding site than the ICOS/B7h interaction (FIG. 6), and ICOS-Fc displays a strong dominant negative effect on several tumor-promoting activities mediated by OPN (FIG. 8). These data confirm that the ICOS-Fc inhibitory activity of the tumor growth is not limited to blocking the interaction between B7h and the endogenous ICOS expressed on T cells.

In view of the experiments performed by the inventors, ICOS-Fc is an antineoplastic drug that can be used either in monotherapy or in combination therapies with other antineoplastic therapies. ICOS-Fc acts by triggering B7h and inhibiting the OPN activity, which are substantial additional effects to the effect of inhibiting the endogenous ICOS/B7h interaction.

Results

Effect of CDNS/ICOS-Fc in the Tumor Growth In Vivo.

C57BL/6 mice carrying palpable subcutaneous B16-F10 tumors were i.v. treated with either the mouse ICOS-Fc, or ICOS-Fc/CDNS or the empty CDNS (100 µg each) or the same volume of PBS as control every 4 days and the tumor growth was monitored every 4 days. Results showed that ICOS-Fc loaded in CDNS (CDNS/ICOS-Fc) substantially inhibited the growth of melanoma cells in the mice, whereas free ICOS-Fc has no effect (FIG. 1).

Effect of CDNS/ICOS-Fc in the Tumor Angiogenesis In Vivo.

To assess the effects of CDNS/ICOS-Fc on tumor angiogenesis, the expression of CD31 in the tumors obtained with B16-F10 cells was evaluated. Results showed that the treatment with CDNS/ICOS-Fc reduced blood vessel formation compared to control mice (PBS) or empty CDNS treated-mice (FIG. 2).

Effect of CDNS/ICOS-Fc on the Immune Response Ex-Vivo.

Figure 3:
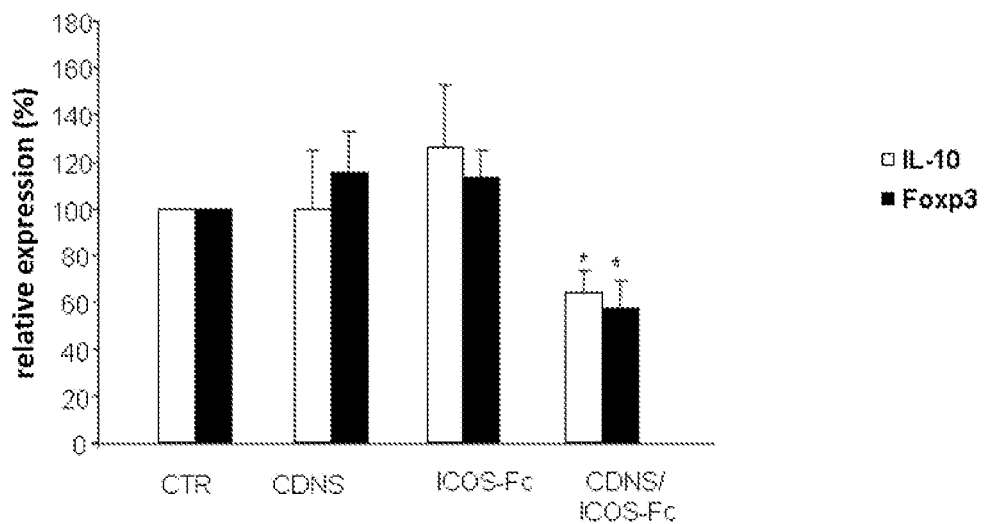
FIG. 3: Effect of CDNS/ICOS-Fc on IL-10 and Foxp3 ex-vivo. Infiltrating cells from tumors were harvested and used for the real time PCR analysis; the data are normalized for the expression in the control mice (control expression PBS group set at 100%; *$p<0.05$).

To assess if the treatment modulates the immune response, infiltrating lymphocytes were obtained from the tumors and the mRNA levels of IL-17A and RORγt (marking TH17 cells), IL-10 and Foxp3 (marking Treg cells) were evaluated by Real Time PCR, since ICOS has a key role in Th17 and Treg cell differentiation. Results showed that treatment with CDNS/ICOS-Fc significantly decreased expression of Foxp3 and IL-10 compared with the levels detected in control mice, whereas free ICOS-Fc and empty CDNS had no effect. In contrast, no significant differences were detected in the expression of RoRγt and IL17A (FIG. 3).

The Effect of CDNS/ICOS-Fc in the Tumor Growth In Vivo does not Depend on the Presence of the Endogenous ICOS.

To assess at which extent the ICOS-Fc anti-tumor effect depends on inhibition of the interaction between B7h and the endogenous ICOS, the effect of CDSN/ICOS-Fc on the B16 tumor growth in ICOS-deficient mice was evaluated. Results showed that ICOS-Fc effectively inhibited the growth of B16 tumors in ICOS-deficient mice (FIG. 4A). The effect on the tumor growth was accompanied by decreased expression of IL-10 and FoxP3 as detected by real time PCR analysis of mRNA extracted from the tissue (FIG. 4B). These data show that the ICOS-Fc effect depends of triggering of B7h and not to antagonism of the B7h binding to the endogenous ICOS.

Cytotoxic Effect of CDNS/ICOS-Fc on Tumor Cells In Vitro

Cell toxicity of the CDNS preparations and free ICOS-Fc was assessed by performing an MTT assay on B16-F10 cells incubated with or without titrated amounts (0.5, 1, 2, 5 µg/ml) of CDNS/ICOS-Fc, or empty CDNS, or free ICOS-Fc. The results detected cell toxicity at the highest doses (30% inhibition at 2 and 5 µg/ml) which was exerted only by CDNS/ICOS-Fc and not by empty CDNS or free ICOS-Fc (FIG. 5).

B7h Binds not Only ICOS but Also OPN

The inventors used two approaches to test the hypothesis that OPN binds to B7h using recombinant B7h-Fc and histidine-tagged OPN or B7h (B7h-his) (FIG. 6). A) ELISA. OPN (or B7h-his) was adsorbed on ELISA plates and then incubated with titrated amounts of B7h-Fc (or OPN) for 1 h. After washing, binding was evaluated with anti-IgG1 mAb (or polyclonal anti-OPN Ab). Results showed a concentration dependent binding of B7h to OPN. Moreover, we showed that the OPN/B7h binding is not inhibited by ICOS-Fc, which indicates that OPN and ICOS-Fc binds different sites of B7h. ICOS-Fc did not show any binding to OPN. B) Pull-down. B7h-Fc was used as a bait protein captured on Sepharose-protein A, and was incubated with OPN for 1 h. After washing, proteins were eluted from the resin and analyzed by Western blot using anti-OPN polyclonal antibodies. Results showed an association between OPN and B7h.

Triggering of B7h by OPN Promotes Migration of Tumor Cell Lines and EC

OPN induces migration of tumor cell lines expressing high levels of B7h (B7h$^{high}$) but not of those expressing low levels (B7h$^{low}$), whereas no difference is found when migration is induced by fetal bovine serum (FBS) (FIG. 7A-B). In B7h$^{low}$ tumor cells, the migratory response to OPN is restored by B7h transfection reinforcing B7h expression whereas, in B7h$^{high}$ HUVEC, it is inhibited by shRNA-mediated silencing of B7h (FIG. 6C-D). The effect is specific since modulation of B7h expression does not affect migration induced by FBS in tumor cells and by VEGF in HUVEC.

ICOS-Fc Exerts Dominant Inhibition of OPN-Induced Migration and Tubulogenesis

In HUVEC, treatment with ICOS-Fc inhibits tubulogenesis induced by OPN but not that induced by VEGF (FIG. 8A).

In tumor cell lines expressing high levels of B7h, treatment with ICOS-Fc inhibits cell migration and adhesion to HUVEC induced by OPN (FIG. 8B).

Effect of PLGA/ICOS-Fc in the tumor growth in vivo. Cell toxicity of the PLGA preparations was assessed by performing an MTT assay on B16-F10 cells incubated with titrated amounts (0.5, 1, 2, 5 µg/ml) of empty PLGA or PLGA/ICOS-Fc NP. Some toxicity was exerted by PLGA/ICOS-Fc NP only at the highest doses, but not by empty PLGA NP or free ICOS-Fc (FIG. 9A).

C57BL/6 mice carrying palpable subcutaneous B16-F10 tumors were i.p. treated with either PLGA/ICOS-Fc or the empty PLGA (100 µg each) or the same volume of PBS as control every 4 days and the tumor growth was monitored every 4 days. Results showed that treatment with PLGA/ICOS-Fc effectively inhibited the growth of B16-F10 tumors compared to both control treatments (FIG. 9B).

Figure 10:
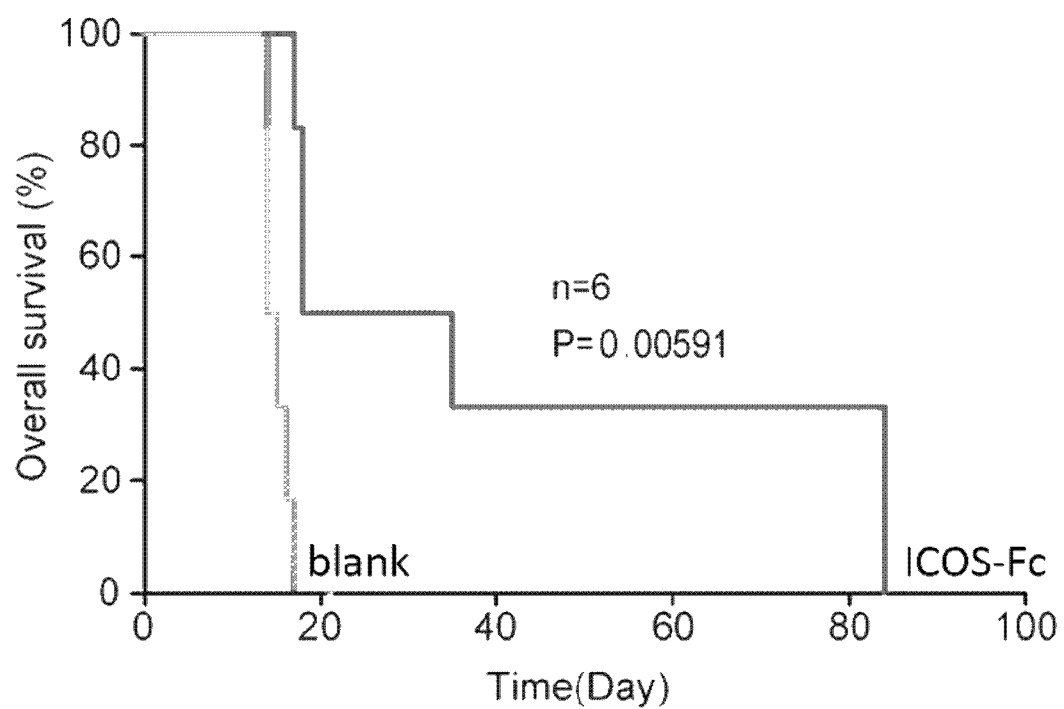
FIG. 10. Effect of PLGA/ICOS-Fc in the survival of athymic mice injected with human glioblastoma cells into the brain. Kaplan-Meier analyses of MD13 tumor-bearing athymic mice treated intraperitoneally by with PLGA alone (blank) (100 µl) or PLGA loaded with human ICOS-Fc (100 µl) after 7 days from implantation and every 7 days. PLGA loading with ICOS-Fc treatment significantly prolonged survival of tumor-bearing mice (blank vs ICOS-Fc in immunocompromised mice, n=6 for all group, P=0.00591, log-rank test).

Athymic mice bearing human glioblastoma in the brain were treated with PLGA-loaded with human ICOS-Fc or empty PLGA one week after implantation of human neuroblastoma cells (MD13) into the brain. Treatment with PLGA/ICOS-Fc significantly prolonged the median survival of tumor-bearing mice (FIG. 10). The treatment with PLGA/ICOS-Fc reduced the tumor formation compared to empty PLGA treated-mice. The effect of PLGA/ICOS-Fc in the tumor growth in vivo does not depend on the presence of the endogenous ICOS$^+$CD4$^+$ T cells, because we evaluated the effect of PLGA/ICOS-Fc in T cell-deficient mice.

Materials and Methods

ICOS and ICOS-Fc Cloning and Production

The extracellular portion of the human or mouse ICOS was cloned into a modified eukaryotic expression vector derived from pCDNA3.1/Hygro(+) plasmid (cod. V870-20, Invitrogen) and reported as p-Minibody (pMB-SV5) by Di Niro R. et al.[25], PubMed ID: 17678525. This vector differs from the original one by: the Kozak sequence (5'CCAC-CATGG 3'—SEQ ID No.: 11) which is required for the initiation of the translation in eukaryotic cells; the secretory leader sequence (5' GCTGGAGCCT-GATCCTCCTGTTCCTCGTCGCTGTGGCTACA 3'—SEQ ID No.: 12) which was introduced to allow the release of the protein in the culture supernatants; the mini intron sequence (5'GGTAAGGGGCT-CACAGTAGCAGGCTTGAGGTCTGGACATATATA TGGGTGACAATGACATCCTTTGCCTTTCTCTC-CACAGGTG 3'—SEQ ID No.: 13) to increase the level of the protein expression. A tag sequence to target the produced-protein was introduced and it is derived from Simian Virus-5 (SV5 tag)(5' GGCAAACCAATCCCAAACC-CACTGCTGGGCCTGGATAGTACT 3'—SEQ ID No.: 14) and it is useful for monoclonal antibody recognition of the protein. This vector allowed to clone the fragments of interest in frame with the coding sequence of the human or mouse constant fragment of the immunoglobulin IgG1 (Fc) domain, having nucleotide sequences set forth in SEQ ID No.: 5 and 9, respectively.

To generate the human ICOS-Fc construct (SEQ ID No.: 3), the nucleotide sequence encoding the extracellular portion of the human ICOS (SEQ ID No.: 4) was amplified with specific primers: ICOS forward BsshII primer (5' TTGGCGCGCATGCCGAAATCAATGGTTCTGCC 3'-SEQ ID No.: 15, Sigma-Genosys, The Woodlands, Tex., USA) and ICOS reverse NheI primer (5' CTAGCTAGCAAGTTGTGATTCATAAATATGC 3'—SEQ ID No.: 16, Sigma-Genosys). The amplified fragments were digested with BssHII (cod. R0199S, New England Biolabs inc, Ipswich, Mass., USA) and NheI (cod. R0131S, New England Biolabs inc) enzymes. The double digested fragments were cloned into the previously described pMB-SV5 plasmid with the coding sequence of the human Fc domain (the human Fc domain has the sequence set forth in SEQ ID No.:5. The nucleotide sequence was determined by sequencing. The nucleotide sequence of the expression vector coding for huICOS-huFc is set forth in SEQ ID No.: 6.

To generate the mouse ICOS-Fc construct (SEQ ID No.: 7), the nucleotide sequence encoding the extracellular portion of the mouse ICOS (SEQ ID No.: 8) was amplified with specific primers: ICOS mouse forward BsshII primer (5' TTGGCGCGCATGCCGAAATCAATGGCTCG 3'—SEQ ID No.: 17, Sigma-Genosys) and ICOS mouse reverse NheI primer (5' CTAGCTAGCTAGCCAGAGCTTCAGCTGGC 3'—SEQ ID No.: 18, Sigma-Genosys). The amplified fragments were digested with BssHII (cod. R0199S, New England Biolabs inc, Ipswich, Mass., USA) and NheI (cod. R0131S, New England Biolabs inc) enzymes. The vector used in this cloning was the pMB-SV5 with the coding sequence of the mouse Fc domain (the mouse Fc domain has the sequence set forth in SEQ ID No.: 9). The double digested fragments were cloned into the previously described pMB-SV5 plasmid. The nucleotide sequence was determined by sequencing. The nucleotide sequence of the expression vector coding for msICOS-msFc is set forth in SEQ ID No.: 10.

The plasmid DNA was transformed into One Shot® TOP10 Chemically Competent *Escherichia Coli* bacterial cells (*E. coli*; cod.C4040-03, Life Technologies, Carlsbad, Calif., USA). The resulting colonies were screened using specific primers: P-Hygro sense (5' CTGCTTACTGGCTATCG 3'—SEQ ID No.: 19, Sigma-Genosys) and P-Hygro antisense (5' CAGATGGCTGGCAACTAG 3'—SEQ ID No.: 20, Sigma-Genosys) and the construct was confirmed by sequencing. Finally, the plasmid DNA was transfected using FreeStyle™ MAX Reagent (cod. 16447100, Life technologies) into Chinese Hamster Ovarian-suspension cell line (CHO-s) (cod. R8/00-07, Invitrogen). The stable clones were obtained thanks to the presence of Hygromycin resistence in the vector; to this end the clones were grown under selection with Hygromycin-B (cod. 10687-010, Invitrogen) at the concentration of 0.2 mg/ml that allow full selection of transfected cells. The cells were grown in serum free IMDM medium (cod. BE12-915F01, Lonza, Basel, Switzerland) and the serum free culture supernatants were purified using Protein G Sepharose™ 4 Fast Flow columns (cod. 17-0618-01, GE Healthcare, Piscataway Township, N.J., USA).

CDNS and CDNS/ICOS-Fc Preparation

A carbonate NS, containing β-cyclodextrins (CDNS; code C4767, Sigma-Aldrich, St. Luis, Mo., USA) as building blocks, cross-linked with a carbonate bridge, was prepared as previously reported[20,21]. Briefly, an amount of anhydrous CD was dissolved in anhydrous dimethylformamide (DMF; code 227056, Sigma-Aldrich, St. Luis, Mo., USA) and allowed to react with carbonyldiimidazole (code 115533, Sigma-Aldrich, St. Luis, Mo., USA) at 90° C. for at least 5 h. Once the reaction was over, a large excess of water was added to destroy the excess of carbonyldiimidazole (code 115533, Sigma-Aldrich, St. Luis, Mo., USA), the solid was recovered by filtration and purified with water. Then, the solid was ground in a mortar and Sohxlet-extracted with ethanol (code 51976, Sigma-Aldrich) to remove residual reaction by-products. The reaction was carried out using a molar excess of crosslinker (e.g. 1:4 cyclodextrin:crosslinker). Following purification, dried NS were stored at 25° C.

β-CDNS is crosslinked with pyromellitic dianhydride (code 412287, Sigma-Aldrich, St. Luis, Mo., USA) to form a carboxylic acid terminated nanoporous material (BNS-Pyro) that form solid particles with a rather spherical morphology and a very high solubilizing power over poorly soluble substances. To obtain BPyro-NS, pyromellitic dianhydride (code 412287, Sigma-Aldrich, St. Luis, Mo., USA) was added to anhydrous cyclodextrin. Synthesis was carried out in anhydrous dimethyl sulfoxide (DMSO, code D1435, Sigma-Aldrich, St. Luis, Mo., USA) at room temperature for 24 h. The molar βNS-Pyro were prepared by crosslinking—CDNS and pyromellitic dianhydride (code 412287, Sigma-Aldrich, St. Luis, Mo., USA) in a 1:8 molar ratio in the presence of ammonia. For biological experiments, the dried preparations were dispersed in a 0.9% NaCl (code S7653, Sigma-Aldrich, St. Luis, Mo., USA) solution at a concentration of 10 mg/ml using an Ultraturrax instrument (IKA, Germany) for 3 min. All reagents were of analytical grade.

The structures of NP were investigated by Raman spectroscopy and imaging methods. Our data by transmission electron microscopy showed that the formed NP have almost spherical morphology with size ranging from 50 to 100 nm with an average of 81±9 nm. The instant results demonstrated that the NS-Pyro NP had not inflammatory effects and did not have any adverse effect on melanoma cells line. The inventors then encapsulated into these βNS-Pyro NP ICOS-Fc. A weighed amount of freeze-dried βNS-Pyro has been dispersed by stirring in an aqueous solution at pH 6.0 containing NaCl (code S7653, Sigma-Aldrich, St. Luis, Mo., USA) and PEG 400 (polyethylene glycol 400, code 202398, Sigma Aldrich, St. Luis, Mo., USA) 3% w/v to obtain an isotonic aqueous nanosuspension containing ICOS-Fc.

PLGA-Nanoparticles (NP) Production

PLGA nanoparticles were prepared by a modified double solvent evaporation method[26]. Briefly 60 mg of PLGA 65:35 crystals (cod. P2066; Sigma-Aldrich, Saint Luis, Mo., USA) were dissolved in 1 ml of dichloromethane (DCM) (cod. 270997; Sigma-Aldrich, St. Luis, Mo., USA) at room temperature. 50 µl of PBS were added to PLGA and the solution was sonicated for 1 min. 5 volumes of 1% PVA (cod. P8136; Sigma-Aldrich, St. Luis, Mo., USA) aqueous solution were carefully added to the resulting emulsion in order to maintain phase separation. A further 2 min sonication was performed to obtain the final emulsion that was evaporated overnight under fume hood, to remove DCM. The resulting nanoparticles were washed 7× in distilled water by centrifugation at 7,000 rpm for 10 min and resuspended in NaCl 0.9%, and stored at 4° C. Nanoparticles containing ICOS-Fc were produced as above by adding ICOS-Fc (1 mg was lyophilized and then resuspended in 50 µl of PBS—phosphate buffer saline), to the PLGA solution dissolved in DCM during the first step of the preparation. The release of ICOS-Fc was evaluated by leaving the nanoparticles in PBS at 37° C., and the proteins released were quantified by the BCA assay (ThermoScientific).

In Vivo Experiments

Female 5-7-wk-old C57BL/6 mice (either wild type cod. 000664-C57BL/6J or ICOS$^{-/-}$ cod. 004859-B6.129P2-Icos$^{tm1Mak}$/J; Charles River Laboratories, Wilmington, Mass., USA) were injected subcutaneously (s.c.) with B16-F10 cells ($10^5$ cells/mouse; cod. CRL-6475; ATTC, Manassas, Va., USA). After 10 days, when tumors were palpable, mice were treated every 4 days with an intravenous (i.v.) injection of either the mouse ICOS-Fc, ICOS-Fc loaded in CDNS (ICOS-Fc/CDNS) or the empty CDNS (100 µg each) or the same volume of PBS as control. The tumor size was measured every 4 days with caliper and mice were sacrificed after 3 weeks. In other experiments, the same treatment protocol was applied by treating mice with either ICOS-Fc loaded in PLGA (ICOS-Fc/PLGA) or the empty PLGA NP (100 µg each) or the same volume of PBS as control.

In other experiments, athymic mice (Balb/c nu/nu; strain code 194, Charles-River) were injected stereotactically into the right striatum with $1 \times 10^4$ human dissociated glioblastoma tumor sphere cells (mesenchymal phenotype) obtained from cell cultures derived from a freshly resected glioma tumor[27], corresponding to stem-like tumor cells, expressing B7h (n=6 per treatment group). After 7 days of tumor challenge, the mice were injected intraperitoneally with 100 µl of PLGA nanoparticles containing ICOS-Fc or empty PLGA. Mice were euthanized when neuropathological signs developed in brain tumor-bearing animals. To obtain the tumor sphere cells, freshly resected glioma tumor samples were dissociated, and the established cells were cultured in defined medium containing DMEM/F12 (cod. 31331-028, Thermo Fisher, Waltham, USA) supplemented with B27 MACS® NeuroBrew®-21 (formerly MACS Supplement B27 PLUS cod. 130-093-566 Miltenyi Biotec, Bergisch Gladbach, Germany) and heparin (2.5 µg/ml, cod. H3149, Sigma-Aldrich, St. Louis, Mo., USA). To enhance proliferation and maintain the stemness, basic fibroblast growth factor (bFGF; 20 ng/ml, cod. 100-18B, Peprotech, London, UK) and epidermal growth factor (EGF; 20 ng/ml, cod. AF-100-15 Peprotech, London. UK) were added to the sphere cultures twice a week[27]. The mice were bred under pathogen-free conditions in the animal facility of the Department of Health Sciences and were treated in accordance with the University Ethical Committee. The study was approved by the Bioethics Committee for Animal Experimentation of the University of Piemonte Orientale and Ministero della Salute (Prot. No. 477/2016-PR).

Real-Time Reverse Transcriptase Polymerase Chain Reaction

The infiltrating cells were obtained from the tumors, and the mRNA levels of IL-17A and RORγt (marking TH17 cells), IL-10 and Foxp3 (marking Treg cells) were evaluated via Real Time PCR. The total RNA was then isolated using TRIzol reagent (cod. 15596026, Thermo Fisher, Waltham, USA). RNA was retrotranscribed using the QuantiTect Reverse Transcription Kit (cod. 205311, Qiagen, Hilden, Germany). Their expressions were evaluated with a gene expression assay (cod. 4453320, Assay-on Demand, Applied Biosystems, Forest City, Calif., USA). The GUSB gene was used to normalize the cDNA amounts. Real Time PCR was performed using the CFX96 System (Bio-Rad Laboratories) in duplicate for each sample in a 10 µl final volume containing 1 µl diluted cDNA, 5 µl TaqMan universal PCR master mix (cod. 4369016 Applied Biosystem, Foster City, Calif.), and 0.5 µl TaqMan Gene Expression Assays (Applied Biosystem). The following assays were used: GUSB, Mm01197698_m1; IL-17A, Mm00439618_m1; RORγt, Mm01261022_m1; IL-10, Mm01288386_m1; Foxp3, Mm00475162_m1. The thermocycler parameters were 95° C. for 10 min, followed by 40 cycles of 95° C. for 15 sec and 60° C. for 1 min. The results were analyzed with a Delta-Delta CT method.

Anti-CD31 Immunofluorescence

Immediately after dissection, tumor samples were embedded in OCT compound (cod. 05-9801 Killik, Bioptica Milano SpA), snap-frozen, and stored at −80° C. until use. Tumor tissues were cut with a cryostat (thickness 5-6 µm) and treated with 4% paraformaldehyde (cod. P6148, Sigma-Aldrich) diluted in PBS for 5 minutes at room temperature to fix the sample on the glass slides. The samples were then blocked with 5% Normal Goat Serum (NGS cod.DY005 R&D System, Minneapolis, USA) in PBS for one hour, in order to block a specific sites to which could bind the primary antibody. To detect CD31 expression, slides were incubated with the primary antibody rabbit anti-CD31 (cod. ab28364 dilution 1:50 Abcam, Cambridge, UK) room temperature for 2 hours. The secondary antibody used was an anti-rabbit Ig Alexa fluor 488-conjugated (cod. A-11008, Thermo Fisher), diluted 1:400. Then the sections were stained with 0.5 mg/ml of the fluorescent dye 4,6-diamidino-2-phenylindole-dihydrochloride (DAPI, cod. D8417, Sigma-Aldrich) for 5 minutes, to color the cell nuclei, and then mounted using Prolong anti-fade mounting medium (Slow Fade AntiFADE Kit, cod. S2828, Molecular Probes Invitrogen). The sections were then observed by a fluorescence microscope (Leica, Italy), and analyzed with the Image Pro Plus Software for micro-imaging 5.0 (Media Cybernetics, version 5.0, Bethesda, Md., USA).

Cell Migration Assay

In the Boyden chamber (BD Biosciences, San Diego, Calif., USA) migration assay, melanoma cells (A2058, cod. CRL-11147, ATCC, Manassas, Va., USA; M14, RRID: CVCL_1395; JR8, RRID:CVCL_5780; PCF-2) were plated onto the apical side of 50 µg/ml matrigel-coated filters (cod. 8.2 mm diameter and 0.3 µm or 0.5 µm pore size; Neuro Probe, Inc.; BIOMAP snc, Milan, Italy; Matrigel Matrix Basement Membrane Cod. L003975 Rif. Cat 354230, SACCO s.r.l., COMO, Italy) in RPMI-1640 (cod.BE12-702F/12, Lonza, Basel, Switzerland) serum-free medium, with or without OPN (10 µg/ml cod. 1433-OP-050, R&D System, Minneapolis, USA) or ICOS-Fc (5 µg/ml). Medium containing 20% FCS (cod. 10270106, Gibco, Gaithersburg, Md., USA) were placed in the basolateral chamber as a positive chemoattractant stimuli. The chamber was incubated at 37° C. under 5% $CO_2$. After 20 h, the cells on the apical side were wiped off with Q-tips. The cells on the bottom of the filter were stained with crystal violet (cod. 61135, Sigma-Aldrich, St. Louis, Mo., USA) and all were counted (fourfold filter) with an inverted microscope (magnification 40×). Data are shown as percentages of the treated cells migration vs the control migration measured for untreated cells.

Cells Adhesion Assay

HUVECs were grown to confluence in 24-well plates (cod. ET3024, Euroclone, Milan, Italy) in complete medium M200 (cod. M200500, Gibco, Gaithersburg, Md., USA) and then treated or not with OPN (10 µg/ml, cod. 1433-OP-050, R&D System, Minneapolis, USA), or ICOS-Fc (5 µg/ml), for 30 min, washed with fresh medium twice, and incubated for 1 h with melanoma cells ($5\times10^4$ cell/well; A2058, cod. CRL-11147, ATCC, Manassas, Va., USA; M14, RRID: CVCL_1395; JR8, RRID:CVCL_5780; PCF-2)). After incubation in the adhesion assay, non-adherent cells were removed by washing three times with M200 medium. The centre of each well was analysed by fluorescence image analysis. Adherent cells were counted by the Image Pro Plus Software for micro-imaging (Media Cybernetics, Bethesda, Md., version 5.0). Data are shown as percentages of the treated cells adhesion vs the control adhesion measured for untreated cells.

Tube-Formation Assay

In the tube-formation assay[28], HUVECs ($2.5\times10^4$/well) were cultured in M200 (cod. M200500, Gibco, Gaithersburg, Md., USA) serum-free medium and seeded onto 48-well plates (cod. ET3048, Euroclone, Milan, Italy) previously coated with 150 µl of growth factor-reduced matrigel (Matrigel Matrix Basement Membrane Cod. L003975 Rif. Cat 354230, SACCO s.r.l., COMO) in the presence of OPN (10 µg/ml, cod. 1433-OP-050, R&D System, Minneapolis, USA), or control medium with VEGF-α (10 ng/ml, cod. 293-VE-010; R&D System, Minneapolis USA). The morphology of the capillary-like structures formed by the HUVECs was analyzed after 6 h of culture using an inverted microscope (Leica Microsystem, Milano, Italy; magnification 10×) and was photographed with a digital camera (Leica Microsystem, Milano, Italy). Tube formation was analyzed and the number of tubes (with branching at both ends) was counted with an imaging system (Image-Pro Plus software for micro-imaging, Media Cybernetics, version5.0, Bethesda, Md., USA). Tube formation was evaluated by counting the total number of tubes in three wells (n=5).

Pull-Down Assay 10 ug of rhB7h2-Fc (cod. 165-B7-100, R&D system, Minneapolis, Minn., USA) and rhOPN (cod. 1433-OP-050/CF, R&D system, Minneapolis, Minn., USA) were join together in PBS at RT on the wheel for 1h, then B7h was precipitated using Sepharose-protein G (cod. 17-0618-01, GE Healthcare, Piscataway, N.J., USA), sample buffer with 20% of β-mercaptoethanol (cod. M-3148, Sigma-Aldrich, Saint Louis, Mo., USA) was used to dissociate the proteins and Western blot was performed. Anti-OPN polyclonal antibodies (cod. MAB14331-SP, R&D system, Minneapolis, Minn., USA) was used to detect OPN on the membrane.

B7h Silencing and Transfection

For B7h silencing experiments, HUVEC cells (1.5*10^5 cells) were seeded on 6 wells plate (cod. ET3006, Euroclone, Milan, Italy) in complete medium IMDM (cod. cod. BE12-915F01, Lonza, Basel, Switzerland) for 24h. To silence the cells, Lipofectamine™ RNAiMAX transfection reagent (cod. 13778030, Life technologies, Carlsbad, Calif., USA) was used with two different siRNA direct B7h (oligo1: ICOSLGHSS177318 (5'-CAGCAGCC-UUCGAGCUGAUACUCAG-3'—SEQ ID No.: 21 and 5'-CUGAGUAUCAGCUCGAAGGCUGCUG-3'—SEQ ID No.: 22) and oligo2: ICOSLGHSS118565 (5'-GGCC-CAACGUGUACUGGAUCAAUAA-3'—SEQ ID No.: 23, and 5'-UUAUUGAUCCAGUACACGUUGGGCC-3'—SEQ ID No.: 24) Life technologies, Carlsbad, Calif., USA) mapping in two different exons. For B7h transfection experiments, A2058 cells (10^6 cells; cod. CRL-11147, ATCC, Manassas, Va., USA) were seeded in 10 cm² dishes (cod. ET2100, Euroclone, Milan, Italy) in complete medium RPMI-1640 (cod.BE12-702F/12, Lonza, Basel, Switzerland. To transfect the cells, 10 µg of DNA and 10 µl of lipofectamine 3000 (cod.L3000001, Life technologies, Carlsbad, Calif., USA) were used. After 24 or 48 hours, the cells silenced or transfected were used for the migration experiments.

ELISA Assay 80 nM of rhOPN (#1433-OP-050/CF, R&D system, Minneapolis, Minn., USA) was adsorbed on Nunc MaxiSorp™ flat-bottom ELISA plate (cod. M9410-1CS, Sigma-Aldrich, St. Louis, Mo., USA) and then incubated with titrated amounts of B7h-Fc (cod. 165-B7-100, R&D system, Minneapolis, Minn., USA) for 1 h with or without 80 nM of rhICOS-Fc. After washing with PBS+0.025% Tryton (cod. T8787, Sigma-Aldrich, St. Louis, Mo., USA), anti-human-IgG1 mAb HRP conjugated (cod. P0214, Dako, Santa Clara, Calif., USA) was added for 1h then TMB substrate (cod. T4444, Sigma-Aldrich, St. Louis, Mo., USA) was used and the reaction was stopped after 2 min with $H_2SO_4$ 2N (cod. 339741, Sigma-Aldrich, St. Louis, Mo., USA) reading the absorbance at 450 nm using Victor-X1 plate reader (Perkin Elmer, Waltham, Mass., USA).

Cell Viability Assay

B16-F10 cells were seeded in 96 well plates at $1\times10^3$ cells/well in RPMI-1640 complete medium. After 24 h the medium was removed and the cells were incubated for 48 h in the medium containing titrated amounts (0.5-5 µg/ml) of CDNS or PLGA NP. After 72 h of incubation, viable cells were evaluated by adding 2,3-bis[2-methoxy-4-nitro-5sulfophenyl]-2H-tetrazolium-5carboxanilide (MTT, Sigma-Aldrich) inner salt reagent (0.5 mg/ml) for 4 h at 37° C. Then, the MTT solution was discarded and formazan crystals were solubilized using 100 µl of DMSO (Sigma-Aldrich). Absorbance was measured at 570 nm in a microplate spectrophotometer (Perkin Elmer, Waltham, Mass., USA). Cell viability was calculated with the following formula: cell viability=Absorbance of sample/absorbance of control×100 (n=5).

Data Analysis

Statistical analyses were performed using Mann-Whitney Test using GraphPad Instat Software (GraphPad Software, San Diego, Calif., USA). Data are expressed as mean±SEM and statistical significance was set at p<0.05 (Mann-Whitney test).

REFERENCES

1. Redoglia V, Dianzani U, Rojo J M, Portolés P, Bragardo M, Wolff H, Buonfiglio D, Bonissoni S, Janeway C A. Characterization of H4: a mouse T lymphocyte activation molecule functionally associated with the CD3/T cell receptor. *Eur J Immunol* 1996; 26:2781-9.
2. Buonfiglio D, Bragardo M, Bonissoni S, Redoglia V, Cauda R, Zupo S, Burgio V L, Wolff H, Franssila K, Gaidano G, Carbone A, Janeway C A Jr, Dianzani U. Characterization of a novel human surface molecule selectively expressed by mature thymocytes, activated T cells and subsets of T cell lymphomas. *Eur J Immunol* 1999; 29:2863-74.
3. Hutloff, A, A M Dittrich, K C Beier, B Eljaschewitsch, R Kraft, I Anagnostopoulos, and R. Kroczek. ICOS is an inducible T cell co-stimulator structurally and functionally related to CD28. *Nature* 1999; 397:263-266.
4. Buonfiglio D, Bragardo M, Redoglia V, Vaschetto R, Bottarel F, Bonissoni S, R. Bensi T, Mezzatesta C, Janeway C A, Dianzani U. The T cell activation molecule H4 and the CD28-like molecule ICOS are identical. *Eur J Immunol* 2000; 30:3463-7.
5. Hedl M, Lahiri A, Ning K, Cho J H, Abraham C. Pattern recognition receptor signaling in human dendritic cells is enhanced by ICOS ligand and modulated by the Crohn's disease ICOSLG risk allele. *Immunity* 2014; 40:734-465.
6. Sharpe A H, Freeman G J. The B7-CD28 superfamily. Nat Rev Immunol 2003; 2:116-26.
7. Nurieva R I. Regulation of immune and autoimmune responses by ICOS-B7h interaction. *Clin Immunol* 2005; 115:19-25.
8. Bauquet A T, Jin H, Paterson A M, Mitsdoerffer M, Ho I C, Sharpe A H, Kuchroo V K. The costimulatory molecule ICOS regulates the expression of c-Maf and IL-21 in the development of follicular T helper cells and TH-17 cells. *Nat Immunol* 2009; 10:167-75.
9. Yong P F, Salzer U, Grimbacher B. The role of costimulation in antibody deficiencies: ICOS and common variable immunodeficiency. *Immunol Rev* 2009; 229:101-13.
10. Mesturini R, Nicola S, Chiocchetti A, Bernardone I S, Castelli L, Bensi T, Ferretti M, Comi C, Dong C, Rojo J M, Yagi J, Dianzani U. ICOS cooperates with CD28, IL-2, and IFN-gamma and modulates activation of human naïve CD4+ T cells. *Eur J Immunol* 2006; 36:2601-12.
11. Mesturini R, Gigliotti C L, Orilieri E, Cappellano G, Soluri M F, Boggio E, Woldetsadik A, Dianzani C, Sblattero D, Chiocchetti A, Yagi J, Rojo J M, Dianzani U. Differential induction of IL-17, IL-10, and IL-9 in human T helper cells by B7h and B7.1. *Cytokine* 2013; 64:322-30.
12. Tang, G., Q. Qin, P. Zhang, G. Wang, M. Liu, Q. Ding, Y. Qin, and Q. Shen. Reverse signaling using an inducible costimulator to enhance immunogenic function of dendritic cells. *Cell Mol Life Sci* 2008; 66:3067-3080.

13. Dianzani C, Minelli R, Mesturini R, Chiocchetti A, Barrera G, Boscolo S, Sarasso C, Gigliotti C L, Sblattero D, Yagi J, Rojo J M, Fantozzi R, Dianzani U. B7h triggering inhibits umbilical vascular endothelial cell adhesiveness to tumor cell lines and polymorphonuclear cells. *J Immunol* 2010; 185: 3970-3979.
14. Dianzani C, Minelli R, Gigliotti C L, Occhipinti S, Giovarelli M, Conti L, Boggio E, Shivakumar Y, Baldanzi G, Malacarne V, Orilieri E, Cappellano G, Fantozzi R, Sblattero D, Yagi J, Rojo J M, Chiocchetti A, Dianzani U. B7h triggering inhibits the migration of tumor cell lines. *J Immunol* 2014; 192:4921-31.
15. Occhipinti S, Dianzani C, Chiocchetti A, Boggio E, Clemente N, Gigliotti C L, Soluri M F, Minelli R, Fantozzi R, Yagi J, Rojo J M, Sblattero D, Giovarelli M, Dianzani U. Triggering of B7h by the inducible costimulator modulates maturation and migration of monocyte-derived dendritic cells. *J Immunol* 2013; 190: 1125-1134.
16. Gigliotti C L, Boggio E, Clemente N, Shivakumar Y, Toth E, Sblattero D, D'Amelio P, Isaia G C, Dianzani C, Yagi J, Rojo J M, Chiocchetti A, Boldorini R, Bosetti M, Dianzani U. ICOS-Ligand Triggering Impairs Osteoclast Differentiation and Function In Vitro and In Vivo. *J Immunol* 2016; 97:3905-3916.
17. Gandalovičová A, Rosel D, Fernandes M, Veselý P, Heneberg P, Čermák V, Petruželka L, Kumar S, Sanz-Moreno V, Brábek J. Migrastatics-Anti-metastatic and Anti-invasion Drugs: Promises and Challenges. *Trends Cancer* 2017; 3:391-406.
18. Steeg P S. Targeting metastasis. *Nat Rev Cancer* 2016; 16:201-18.
19. Morimoto J, Kon S, Matsui Y, Uede T. Osteopontin; as a target molecule for the treatment of inflammatory diseases. *Curr Drug Targets* 2010; 11:494-505.
20. Swaminathan S, Pastero L, Serpe L, Trotta F, Vavia P, Aquilano D, Trotta M, Zara G, Cavalli R. Cyclodextrin-based nanosponges encapsulating camptothecin: physico-chemical characterization, stability and cytotoxicity. *Eur J Pharm Biopharm.* 2010; 74:193-201.
21. Trotta F, Zanetti M, Cavalli R. Cyclodextrin-based nanosponges as drug carriers. *J. Org. Chem.* 2012; 8:2091-2099.
22. Szejtl J. Introduction and general overview of cyclodextrin chemistry. *Chem. Rev.* 1998; 98:1743-1754.
23. Swaminathan S, Cavalli R, Trotta F. Cyclodextrin-50 based nanosponges: a versatile platform for cancer nanotherapeutics development. *Interdiscip Rev Nanomed Nanobiotechnol.* 2016; 8:579-601.
24. Trotta F, Dianzani C, Caldera F, Mognetti B, Cavalli R. The application of nanosponges to cancer drug delivery. *Expert Opin Drug Deliv.* 2014; 11:931-941.
25. Di Niro R, Ziller F, Florian F, Crovella S, Stebel M, Bestagno M, Burrone O, Bradbury A R, Secco P, Marzari R, Sblattero D. Construction of miniantibodies for the in vivo study of human autoimmune diseases in animal models. BMC Biotechnol. 2007 Aug. 1; 7:46.
26. Zhou X, Liu B, Yu X, Zha X, Zhang X, Wang X, Jin Y, Wu Y, Chen Y, Shan Y, Chen Y, Liu J, Kong W, Shen J. Controlled release of PEI/DNA complexes from PLGA microspheres as a potent delivery system to enhance immune response to HIV vaccine DNA prime/MVA boost regime. Eur J Pharm Biopharm 2008; 68:589-95.
27. Kim S H, Ezhilarasan R, Phillips E, Gallego-Perez D, Sparks A, Taylor D, Ladner K, Furuta T, Sabit H, Chhipa R, Cho J H, Mohyeldin A, Beck S, Kurozumi K, Kuroiwa T, Iwata R, Asai A, Kim J, Sulman E P, Cheng S Y, Lee L J, Nakada M, Guttridge D, DasGupta B, Goidts V, Bhat K P, Nakano I. Serine/Threonine Kinase MLK4 Determines Mesenchymal Identity in Glioma Stem Cells in an NF-kappaB-dependent Manner. Cancer Cell, 2016. 29(2): 201-13.
28. DeCicco-Skinner K L, Henry G H, Cataisson C, Tabib T, Gwilliam J C, Watson N J, Bullwinkle E M, Falkenburg L, O'Neill R C, Morin A, Wiest J S. Endothelial cell tube formation assay for the in vitro study of angiogenesis. J Vis Exp. 2014 Sep. 1; (91):e51312.

The invention claimed is:

1. A method of treatment comprising administering to a subject in need thereof suffering from an established tumor a composition comprising an active agent loaded into or onto a biocompatible micro-or nano-carrier, wherein the active agent consists of a ligand of receptor B7h, wherein the ligand loaded into or onto the biocompatible micro-or nano-carrier is capable of exerting cell toxicity in an in vitro B16-F10 cell viability assay, and wherein the ligand comprises
    a) a human ICOS protein having the amino acid sequence as set forth in SEQ ID No.: 1 or a B7h binding portion thereof;
    b) a human ICOS extracellular domain having the amino acid sequence as set forth in SEQ ID No.: 2 or a B7h binding portion thereof; or
    c) a polypeptide having at least 95% sequence identity to the amino acid sequence of the human ICOS protein or B7h binding portion thereof according to a) or to the amino acid sequence of the human ICOS extracellular domain or B7h binding portion thereof according to b), wherein the polypeptide is capable of binding to receptor B7h.

2. The method according to claim 1, wherein the ligand is hyperglycosylated or conjugated to mannose residues.

3. The method according to claim 1, wherein the ligand loaded into or onto a biocompatible micro-or nano-carrier is administered by injection or infusion.

4. The method according to claim 1, wherein the ligand is fused or conjugated to a stabilizing molecule.

5. The method according to claim 4, wherein the stabilizing molecule is selected from: a human Fc antibody domain, polyethylene glycols, poly-L-lysine citramide, styrenemaleic acid anhydride, and polyhydroxypropylmetacrylamide.

6. The method according to claim 1, wherein the ligand comprises the amino acid sequence as set forth in SEQ ID No.: 3.

7. The method according to claim 1, wherein the biocompatible micro-or nano-carrier is selected from micro-or nano-particles, micro-or nano-capsules, micro-or nano-vesicles, micro-or nano-bubbles, nanoemulsions, nanosuspensions, nanohydrogels, micelles, dendrimers, quantum dots, liposomes, and carbon derivatives.

8. The method according to claim 7, wherein the micro-or nano-particles are made of cyclodextrin polymer, poly (lactide-co-glycolic acid), polycaprolactone, (PCL), polylactic acid (PLA), poly (glycolide), chitosan, alginate, starch, collagen, albumin, silica or metal.

9. The method according to claim 7, wherein the micro-or nano-particles are made of cyclodextrin polymer or poly (lactide-co-glycolic acid).

10. The method according to claim 9, wherein the tumor is melanoma or glioblastoma.

11. A method of treatment comprising administering to a subject in need thereof suffering from an established tumor a pharmaceutical composition comprising an active agent loaded into or onto a biocompatible micro-or nano-carrier, wherein the active agent consists of a ligand of receptor B7h, wherein the ligand loaded into or onto a biocompatible micro-or nano-carrier is capable of exerting cell toxicity in an in vitro B16-F10 cell viability assay, and wherein the ligand comprises
    a) a human ICOS protein having the amino acid sequence as set forth in SEQ ID No.: 1 or a B7h binding portion thereof;
    b) a human ICOS extracellular domain having the amino acid sequence as set forth in SEQ ID No.: 2 or a B7h binding portion thereof; or
    c) a polypeptide having at least 95% sequence identity to the amino acid sequence of the human ICOS protein or B7h binding portion thereof according to a) or to the amino acid sequence of the human ICOS extracellular domain or B7h binding portion thereof according to b), wherein the polypeptide is capable of binding to receptor B7h.

12. The method according to claim 11, wherein the ligand is fused or conjugated to a stabilizing molecule.

13. The method according to claim 11, wherein the ligand comprises an amino acid sequence as set forth in SEQ ID No.: 3.

14. The method according to claim 11, wherein the biocompatible micro-or nano-carrier is selected from micro-or nano-particles, micro-or nano-capsules, micro-or nano-vesicles, micro-or nano-bubbles, nanoemulsions, nanosuspensions, nanohydrogels, micelles, dendrimers, quantum dots, liposomes, and carbon derivatives.

15. The method according to claim 11, wherein the micro-or nano-particles are made of cyclodextrin polymer or poly (lactide-co-glycolic acid).

16. The method according to claim 15, wherein the tumor is melanoma or glioblastoma.

17. A method of inhibiting tumor angiogenesis comprising administering to a subject in need thereof suffering from a tumor a ligand of receptor B7h, wherein the ligand of B7h receptor has been loaded into or onto a biocompatible micro-or nano-carrier, wherein the ligand loaded into or onto the biocompatible micro-or nano-carrier is capable of exerting cell toxicity in an in vitro B16-F10 cell viability assay, and wherein the ligand comprises
    a) a human ICOS protein having the amino acid sequence as set forth in SEQ ID No.: 1 or a B7h binding portion thereof;
    b) a human ICOS extracellular domain having the amino acid sequence as set forth in SEQ ID No.: 2 or a B7h binding portion thereof; or
    c) a polypeptide having at least 95% sequence identity to the amino acid sequence of the human ICOS protein or B7h binding portion thereof according to a) or to the amino acid sequence of the human ICOS extracellular domain or B7h binding portion thereof according to b), wherein the polypeptide is capable of binding to receptor B7h.

18. The method according to claim 17, wherein the ligand is fused or conjugated to a stabilizing molecule selected from the group consisting of: a human Fc antibody domain, polyethylene glycols, poly-L-lysine citramide, styrenemaleic acid anhydride, and polyhydroxypropylmetacrylamide.

19. The method according to claim 17, wherein the ligand comprises the amino acid sequence as set forth in SEQ ID No.: 3.

20. The method according to claim 17, wherein the micro-or nano-particles are made of cyclodextrin polymer, poly (lactide-co-glycolic acid), polycaprolactone, (PCL), polylactic acid (PLA), poly (glycolide), chitosan, alginate, starch, collagen, albumin, silica or metal.

21. The method according to claim 17, wherein the tumor is melanoma or glioblastoma.

* * * * *

```
SEQUENCE LISTING

<160> NUMBER OF SEQ ID NOS: 24

<210> SEQ ID NO 1
<211> LENGTH: 199
<212> TYPE: PRT
<213> ORGANISM: homo sapiens

<400> SEQUENCE: 1

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110
```

```
Ile Phe Asp Pro Pro Pro Phe Lys Val Thr Leu Thr Gly Gly Tyr Leu
            115                 120                 125

His Ile Tyr Glu Ser Gln Leu Cys Cys Gln Leu Lys Phe Trp Leu Pro
            130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Val His Asp Pro
            165                 170                 175

Asn Gly Glu Tyr Met Phe Met Arg Ala Val Asn Thr Ala Lys Lys Ser
            180                 185                 190

Arg Leu Thr Asp Val Thr Leu
            195

<210> SEQ ID NO 2
<211> LENGTH: 115
<212> TYPE: PRT
<213> ORGANISM: homo sapiens

<400> SEQUENCE: 2

Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
            35                  40                  45

Lys Gly Ser Gly Asn Thr Val Ser Ile Lys Ser Leu Lys Phe Cys His
        50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
            100                 105                 110

Ser Gln Leu
        115

<210> SEQ ID NO 3
<211> LENGTH: 348
<212> TYPE: PRT
<213> ORGANISM: artificial
<220> FEATURE:
<223> OTHER INFORMATION: human ICOS-Human Fc

<400> SEQUENCE: 3

Gly Ala His Gly Glu Ile Asn Gly Ser Ala Asn Tyr Glu Met Phe Ile
1               5                   10                  15

Phe His Asn Gly Gly Val Gln Ile Leu Cys Lys Tyr Pro Asp Ile Val
            20                  25                  30

Gln Gln Phe Lys Met Gln Leu Leu Lys Gly Gly Gln Ile Leu Cys Asp
            35                  40                  45

Leu Thr Lys Thr Lys Gly Ser Gly Asn Thr Val Ser Ile Lys Ser Leu
        50                  55                  60

Lys Phe Cys His Ser Gln Leu Ser Asn Asn Ser Val Ser Phe Phe Leu
65                  70                  75                  80

Tyr Asn Leu Asp His Ser His Ala Asn Tyr Tyr Phe Cys Asn Leu Ser
                85                  90                  95

Ile Phe Asp Pro Pro Pro Phe Lys Val Thr Leu Thr Gly Gly Tyr Leu
```

```
                        100                 105                 110
His Ile Tyr Glu Ser Gln Leu Ala Ser Asp Lys Thr His Thr Cys Pro
            115                 120                 125

Pro Cys Pro Ala Pro Glu Leu Leu Gly Gly Pro Ser Val Phe Leu Phe
            130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
            195                 200                 205

Val Leu His Gln Asp Trp Leu Asn Gly Lys Glu Tyr Lys Cys Lys Val
            210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
            275                 280                 285

Glu Asn Asn Tyr Lys Thr Thr Pro Pro Val Leu Asp Ser Asp Gly Ser
290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345
```

<210> SEQ ID NO 4
<211> LENGTH: 345
<212> TYPE: DNA
<213> ORGANISM: homo sapiens

<400> SEQUENCE: 4

```
gaaatcaatg gttctgccaa ttatgagatg tttatatttc acaacggagg tgtacaaatt      60
ttatgcaaat atcctgacat tgtccagcaa tttaaaatgc agttgctgaa agggggggcaa    120
atactctgcg atctcactaa gacaaaagga agtggaaaca cagtgtccat taagagtctg    180
aaattctgcc attctcagtt atccaacaac agtgtctctt ttttttctata caacttggac    240
cattctcatg ccaactatta cttctgcaac ctatcaattt tgatcctcc tccttttaaa     300
gtaactctta caggaggata tttgcatatt tatgaatcac aactt                    345
```

<210> SEQ ID NO 5
<211> LENGTH: 681
<212> TYPE: DNA
<213> ORGANISM: homo sapiens

<400> SEQUENCE: 5

```
gacaaaactc acacatgccc accgtgccca gcacctgaac tcctgggggg accgtcagtc      60
ttcctcttcc ccccaaaacc caaggacacc ctcatgatct cccggacccc tgaggtcaca    120
```

| | |
|---|---|
| tgcgtggtgg tggacgtgag ccacgaagac cctgaggtca agttcaactg gtacgtggac | 180 |
| ggcgtggagg tgcataatgc caagacaaag ccgcgggagg agcagtacaa cagcacgtac | 240 |
| cgtgtggtca gcgtcctcac cgtcctgcac caggactggc tgaatggcaa ggagtacaag | 300 |
| tgcaaggtct ccaacaaagc cctcccagcc cccatcgaga aaaccatctc caaagccaaa | 360 |
| gggcagcccc gagaaccaca ggtgtacacc ctgcccccat cccgggagga gatgaccaag | 420 |
| aaccaggtca gcctgacctg cctggtcaaa ggcttctatc ccagcgacat cgccgtggag | 480 |
| tgggagagca atgggcagcc ggagaacaac tacaagacca cgcctcccgt gctggactcc | 540 |
| gacggctcct tcttcctcta tagcaagctc accgtggaca agagcaggtg gcagcagggg | 600 |
| aacgtcttct catgctccgt gatgcatgag gctctgcaca accactacac gcagaagagc | 660 |
| ctctccctgt ccccgggtaa a | 681 |

<210> SEQ ID NO 6
<211> LENGTH: 6729
<212> TYPE: DNA
<213> ORGANISM: artificial
<220> FEATURE:
<223> OTHER INFORMATION: vector encoding huICOS-huFc

<400> SEQUENCE: 6

| | |
|---|---|
| gacggatcgg gagatctccc gatccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctgtctaga | 900 |
| tgccaccatg ggctggagcc tgatcctcct gttcctcgtc gctgtggcta caggtaaggg | 960 |
| gctcacagta gcaggcttga ggtctggaca tatatatggg tgacaatgac atccactttg | 1020 |
| cctttctctc cacaggtggc gcgcatgccg aaatcaatgg ttctgccaat tatgagatgt | 1080 |
| ttatatttca caacggaggt gtacaaattt tatgcaaata cctgacattt gtccagcaat | 1140 |
| ttaaaatgca gttgctgaaa ggggggcaaa tactctgcga tctcactaag acaaaaggaa | 1200 |
| gtggaaacac agtgtccatt aagagtctga aattctgcca ttctcagtta tccaacaaca | 1260 |
| gtgtctcttt ttttctatac aacttggacc attctcatgc caactattac ttctgcaacc | 1320 |
| tatcaatttt tgatcctcct ccttttaaag taactcttac aggaggatat ttgcatattt | 1380 |
| atgaatcaca acttgctagc gacaaaaactc acacatgccc accgtgccca gcacctgaac | 1440 |
| tcctgggggg accgtcagtc ttcctcttcc ccccaaaacc caaggacacc ctcatgatct | 1500 |

```
cccggacccc tgaggtcaca tgcgtggtgg tggacgtgag ccacgaagac cctgaggtca    1560
agttcaactg gtacgtggac ggcgtggagg tgcataatgc caagacaaag ccgcgggagg    1620
agcagtacaa cagcacgtac cgtgtggtca gcgtcctcac cgtcctgcac caggactggc    1680
tgaatggcaa ggagtacaag tgcaaggtct ccaacaaagc cctcccagcc cccatcgaga    1740
aaaccatctc caaagccaaa gggcagcccc gagaaccaca ggtgtacacc ctgccccat     1800 cccggggagga tgaccaag aaccaggtca gcctgacctg cctggtcaaa ggcttctatc    1860
ccagcgacat cgccgtggag tgggagagca atgggcagcc ggagaacaac tacaagacca    1920
cgcctcccgt gctggactcc gacggctcct tcttcctcta tagcaagctc accgtggaca    1980
agagcaggtg gcagcagggg aacgtcttct catgctccgt gatgcatgag gctctgcaca    2040
accactacac gcagaagagc ctctccctgt ccccgggtaa aactagtggc aaaccaatcc    2100
caaacccact gctgggcctg gatagtactt aaaagcttaa acccgctgat cagcctcgac    2160
tgtgccttct agttgccagc catctgttgt ttgcccctcc cccgtgcctt ccttgaccct    2220
ggaaggtgcc actcccactg tcctttccta ataaaatgag gaaattgcat cgcattgtct    2280
gagtaggtgt cattctattc tggggggtgg ggtggggcag gacagcaagg gggaggattg    2340
ggaagacaat agcaggcatg ctggggatgc ggtgggctct atggcttctg aggcggaaag    2400
aaccagctgg ggctctaggg ggtatcccca cgcgccctgt agcggcgcat taagcgcggc    2460
gggtgtggtg gttacgcgca gcgtgaccgc tacacttgcc agcgccctag cgcccgctcc    2520
tttcgctttc ttcccttcct ttctcgccac gttcgccggc tttccccgtc aagctctaaa    2580
tcgggggctc cctttagggt tccgatttag tgctttacgg cacctcgacc ccaaaaaact    2640
tgattagggt gatggttcac gtagtgggcc atcgccctga tagacggttt ttcgcccttt    2700
gacgttggag tccacgttct ttaatagtgg actcttgttc caaactggaa caacactcaa    2760
ccctatctcg gtctattctt ttgatttata agggattttg ccgatttcgg cctattggtt    2820
aaaaaatgag ctgatttaac aaaaatttaa cgcgaattaa ttctgtggaa tgtgtgtcag    2880
ttagggtgtg gaaagtcccc aggctccca gcaggcagaa gtatgcaaag catgcatctc     2940
aattagtcag caaccaggtg tggaaagtcc ccaggctccc cagcaggcag aagtatgcaa    3000
agcatgcatc tcaattagtc agcaaccata gtcccgcccc taactccgcc catcccgccc    3060
ctaactccgc ccagttccgc ccattctccg ccccatggct gactaatttt ttttatttat    3120
gcagaggccg aggccgcctc tgcctctgag ctattccaga agtagtgagg aggcttttt     3180 ggaggcctag gcttttgcaa aaagctcccg ggagcttgta tatccatttt cggatctgat    3240
cagcacgtga tgaaaaagcc tgaactcacc gcgacgtctg tcgagaagtt tctgatcgaa    3300
aagttcgaca gcgtctccga cctgatgcag ctctcggagg gcgaagaatc tcgtgctttc    3360
agcttcgatg taggagggcg tggatatgtc ctgcgggtaa atagctgcgc cgatggtttc    3420
tacaaagatc gttatgttta tcggcacttt gcatcggccg cgctcccgat tccggaagtg    3480
cttgacattg gggaattcag cgagagcctg acctattgca tctcccgccg tgcacagggt    3540
gtcacgttgc aagacctgcc tgaaaccgaa ctgcccgctg ttctgcagcc ggtcgcggag    3600
gccatggatg cgatcgctgc ggccgatctt agccagacga gcgggttcgg cccattcgga    3660
ccgcaaggaa tcggtcaata cactacatgg cgtgatttca tatgcgcgat tgctgatccc    3720
catgtgtatc actggcaaac tgtgatggac gacaccgtca gtgcgtccgt cgcgcaggct    3780
ctcgatgagc tgatgctttg ggccgaggac tgccccgaag tccggcacct cgtgcacgcg    3840
```

-continued

```
gatttcggct ccaacaatgt cctgacggac aatggccgca taacagcggt cattgactgg    3900
agcgaggcga tgttcgggga ttcccaatac gaggtcgcca acatcttctt ctggaggccg    3960
tggttggctt gtatggagca gcagacgcgc tacttcgagc ggaggcatcc ggagcttgca    4020
ggatcgccgc ggctccgggc gtatatgctc cgcattggtc ttgaccaact ctatcagagc    4080
ttggttgacg gcaatttcga tgatgcagct tgggcgcagg gtcgatgcga cgcaatcgtc    4140
cgatccggag ccgggactgt cgggcgtaca caaatcgccc gcagaagcgc ggccgtctgg    4200
accgatggct gtgtagaagt actcgccgat agtggaaacc gacgcccag cactcgtccg     4260 agggcaaagg aatagcacgt gctacgagat ttcgattcca ccgccgcctt ctatgaaagg    4320
ttgggcttcg gaatcgtttt ccgggacgcc ggctggatga tcctccagcg cggggatctc    4380
atgctggagt tcttcgccca ccccaacttg tttattgcag cttataatgg ttacaaataa    4440
agcaatagca tcacaaattt cacaaataaa gcatttttt cactgcattc tagttgtggt     4500
ttgtccaaac tcatcaatgt atcttatcat gtctgtatac cgtcgacctc tagctagagc    4560
ttggcgtaat catggtcata gctgtttcct gtgtgaaatt gttatccgct cacaattcca    4620
cacaacatac gagccggaag cataaagtgt aaagcctggg gtgcctaatg agtgagctaa    4680
ctcacattaa ttgcgttgcg ctcactgccc gctttccagt cgggaaacct gtcgtgccag    4740
ctgcattaat gaatcggcca acgcgcgggg agaggcggtt tgcgtattgg gcgctcttcc    4800
gcttcctcgc tcactgactc gctgcgctcg gtcgttcggc tgcggcgagc ggtatcagct    4860
cactcaaagg cggtaatacg gttatccaca gaatcagggg ataacgcagg aaagaacatg    4920
tgagcaaaag gccagcaaaa ggccaggaac cgtaaaaagg ccgcgttgct ggcgtttttc    4980
cataggctcc gcccccctga cgagcatcac aaaaatcgac gctcaagtca gaggtggcga    5040
aacccgacag gactataaag ataccaggcg tttccccctg gaagctccct cgtgcgctct    5100
cctgttccga ccctgccgct taccggatac ctgtccgcct ttctcccttc gggaagcgtg    5160
gcgctttctc atagctcacg ctgtaggtat ctcagttcgg tgtaggtcgt tcgctccaag    5220
ctgggctgtg tgcacgaacc ccccgttcag cccgaccgct gcgccttatc cggtaactat    5280
cgtcttgagt ccaacccggt aagacacgac ttatcgccac tggcagcagc cactggtaac    5340
aggattagca gagcgaggta tgtaggcggt gctacagagt tcttgaagtg gtggcctaac    5400
tacggctaca ctagaagaac agtatttggt atctgcgctc tgctgaagcc agttaccttc    5460
ggaaaaagag ttggtagctc ttgatccggc aaacaaacca ccgctggtag cggtttttt     5520 gtttgcaagc agcagattac gcgcagaaaa aaaggatctc aagaagatcc tttgatcttt    5580
tctacggggt ctgacgctca gtggaacgaa aactcacgtt aagggatttt ggtcatgaga    5640
ttatcaaaaa ggatcttcac ctagatcctt taaattaaa aatgaagttt taaatcaatc     5700
taaagtatat atgagtaaac ttggtctgac agttaccaat gcttaatcag tgaggcacct    5760
atctcagcga tctgtctatt tcgttcatcc atagttgcct gactccccgt cgtgtagata    5820
actacgatac gggagggctt accatctggc cccagtgctg caatgatacc gcgagaccca    5880
cgctcaccgg ctccagattt atcagcaata aaccagccag ccggaagggc cgagcgcaga    5940
agtggtcctg caactttatc cgcctccatc cagtctatta attgttgccg ggaagctaga    6000
gtaagtagtt cgccagttaa tagtttgcgc aacgttgttg ccattgctac aggcatcgtg    6060
gtgtcacgct cgtcgtttgg tatggcttca ttcagctccg gttcccaacg atcaaggcga    6120
gttacatgat cccccatgtt gtgcaaaaaa gcggttagct ccttcggtcc tccgatcgtt    6180
gtcagaagta agttggccgc agtgttatca ctcatggtta tggcagcact gcataattct    6240
```

```
cttactgtca tgccatccgt aagatgcttt tctgtgactg gtgagtactc aaccaagtca    6300
ttctgagaat agtgtatgcg gcgaccgagt tgctcttgcc cggcgtcaat acgggataat    6360
accgcgccac atagcagaac tttaaaagtg ctcatcattg gaaaacgttc ttcggggcga    6420
aaactctcaa ggatcttacc gctgttgaga tccagttcga tgtaacccac tcgtgcaccc    6480
aactgatctt cagcatcttt tactttcacc agcgtttctg ggtgagcaaa acaggaagg    6540 caaaatgccg caaaaaggg aataagggcg cacggaaat gttgaatact catactcttc    6600 cttttttcaat attattgaag catttatcag ggttattgtc tcatgagcgg atacatattt    6660
gaatgtattt agaaaaataa acaaataggg gttccgcgca catttccccg aaaagtgcca    6720
cctgacgtc                                                             6729
```

<210> SEQ ID NO 7
<211> LENGTH: 352
<212> TYPE: PRT
<213> ORGANISM: artificial
<220> FEATURE:
<223> OTHER INFORMATION: msICOS-msFc

<400> SEQUENCE: 7

```
Gly Ala His Gly Glu Ile Asn Gly Ser Ala Asp His Arg Met Phe Ser
1               5                   10                  15

Phe His Asn Gly Gly Val Gln Ile Ser Cys Lys Tyr Pro Glu Thr Val
            20                  25                  30

Gln Gln Leu Lys Met Arg Leu Phe Arg Glu Arg Glu Val Leu Cys Glu
        35                  40                  45

Leu Thr Lys Thr Lys Gly Ser Gly Asn Ala Val Ser Ile Lys Asn Pro
    50                  55                  60

Met Leu Cys Leu Tyr His Leu Ser Asn Asn Ser Val Ser Phe Phe Leu
65                  70                  75                  80

Asn Asn Pro Asp Ser Ser Gln Gly Ser Tyr Tyr Phe Cys Ser Leu Ser
                85                  90                  95

Ile Phe Asp Pro Pro Pro Phe Gln Glu Arg Asn Leu Ser Gly Gly Tyr
            100                 105                 110

Leu His Ile Tyr Glu Ser Gln Leu Cys Cys Gln Leu Lys Leu Trp Leu
        115                 120                 125

Ala Ser Gly Cys Lys Pro Cys Ile Cys Thr Val Pro Glu Val Ser Ser
    130                 135                 140

Val Phe Ile Phe Pro Pro Lys Pro Lys Asp Val Leu Thr Ile Thr Leu
145                 150                 155                 160

Thr Pro Lys Val Thr Cys Val Val Asp Ile Ser Lys Asp Asp Pro
                165                 170                 175

Glu Val Gln Phe Ser Trp Phe Val Asp Asp Val Glu Val His Thr Ala
            180                 185                 190

Gln Thr Lys Pro Arg Glu Glu Gln Ile Asn Ser Thr Phe Arg Ser Val
        195                 200                 205

Ser Glu Leu Pro Ile Met His Gln Asp Trp Leu Asn Gly Lys Glu Phe
    210                 215                 220

Lys Cys Arg Val Asn Ser Ala Ala Phe Pro Ala Pro Ile Glu Lys Thr
225                 230                 235                 240

Ile Ser Lys Thr Lys Gly Arg Pro Lys Ala Pro Gln Val Tyr Thr Ile
                245                 250                 255

Pro Pro Pro Lys Glu Gln Met Ala Lys Asp Lys Val Ser Leu Thr Cys
            260                 265                 270
```

Met Ile Thr Asn Phe Phe Pro Glu Asp Ile Thr Val Glu Trp Gln Trp
        275                 280                 285

Asn Gly Gln Pro Ala Glu Asn Tyr Lys Asn Thr Gln Pro Ile Met Asp
290                 295                 300

Thr Asp Gly Ser Tyr Phe Val Tyr Ser Lys Leu Asn Val Gln Lys Ser
305                 310                 315                 320

Asn Trp Glu Ala Gly Asn Thr Phe Thr Cys Ser Val Leu His Glu Gly
                325                 330                 335

Leu His Asn His His Thr Glu Lys Ser Leu Ser His Ser Pro Gly Lys
                340                 345                 350

<210> SEQ ID NO 8
<211> LENGTH: 372
<212> TYPE: DNA
<213> ORGANISM: mus musculus

<400> SEQUENCE: 8
gaaatcaatg gctcggccga tcataggatg ttttcatttc acaatggagg tgtacagatt     60
tcttgtaaat accctgagac tgtccagcag ttaaaaatgc gattgttcag agagagagaa    120
gtcctctgcg aactcaccaa gaccaaggga agcggaaatg cggtgtccat caagaatcca    180
atgctctgtc tatatcatct gtcaaacaac agcgtctctt ttttcctaaa caacccagac    240
agctcccagg gaagctatta cttctgcagc ctgtccattt tgacccacc tcctttcaa     300 gaaaggaacc ttagtggagg atatttgcat atttatgaat cccagctctg ctgccagctg    360
aagctctggc ta                                                        372

<210> SEQ ID NO 9
<211> LENGTH: 666
<212> TYPE: DNA
<213> ORGANISM: mus musculus

<400> SEQUENCE: 9
ggttgtaagc cttgcatatg tacagtccca gaagtatcat ctgtcttcat cttcccccca     60
aagcccaagg atgtgctcac cattactctg actcctaagg tcacgtgtgt tgtggtagac    120
atcagcaagg atgatcccga ggtccagttc agctggtttg tagatgatgt ggaggtgcac    180
acagctcaga cgaaacccg ggaggagcag atcaacagca ctttccgttc agtcagtgaa    240
cttcccatca tgcaccagga ctggctcaat ggcaaggagt tcaaatgcag ggtcaacagt    300
gcagctttcc ctgcccccat cgagaaaacc atctccaaaa ccaaaggcag accgaaggct    360
ccacaggtgt acaccattcc acctcccaag gagcagatgg ccaaggataa agtcagtctg    420
acctgcatga taacaaactt cttccctgaa gacattactg tggagtggca gtggaatggg    480
cagccagcgg agaactacaa gaacactcag cccatcatgg acacagatgg ctcttacttc    540
gtctacagca agctcaatgt gcagaagagc aactgggagg caggaaatac tttcacctgc    600
tctgtgttac atgagggcct gcacaaccac catactgaga gagcctctc ccactctcct    660 ggtaaa                                                               666

<210> SEQ ID NO 10
<211> LENGTH: 6719
<212> TYPE: DNA
<213> ORGANISM: artificial
<220> FEATURE:
<223> OTHER INFORMATION: vector encoding msICOS-msFc contruct

<400> SEQUENCE: 10

-continued

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctgtctaga     900
tgccaccatg ggctggagcc tgatcctcct gttcctcgtc gctgtggcta caggtaaggg     960
gctcacagta gcaggcttga ggtctggaca tatatatggg tgacaatgac atccactttg    1020
cctttctctc cacaggtggc gcgcatgccg aaatcaatgg ctcggccgat cataggatgt    1080
tttcatttca caatggaggt gtacagattt cttgtaaata ccctgagact gtccagcagt    1140
taaaaatgcg attgttcaga gagagagaag tcctctgcga actcaccaag accaagggaa    1200
gcggaaatgc ggtgtccatc aagaatccaa tgctctgtct atatcatctg tcaaacaaca    1260
gcgtctcttt tttcctaaac aacccagaca gctcccaggg aagctattac ttctgcagcc    1320
tgtccatttt tgacccacct ccttttcaag aaaggaacct tagtggagga tatttgcata    1380
tttatgaatc ccagctctgg ctagcggttg taagccttgc atatgtacag tcccagaagt    1440
atcatctgtc ttcatcttcc ccccaaagcc caaggatgtg ctcaccatta ctctgactcc    1500
taaggtcacg tgtgttgtgg tagacatcag caaggatgat cccgaggtcc agttcagctg    1560
gtttgtagat gatgtggagg tgcacacagc tcagacgaaa ccccgggagg agcagatcaa    1620
cagcactttc cgttcagtca gtgaacttcc catcatgcac caggactggc tcaatggcaa    1680
ggagttcaaa tgcagggtca acagtgcagc ttttcctgcc cccatcgaga aaaccatctc    1740
caaaaccaaa ggcagaccga aggctccaca ggtgtacacc attccacctc caaggagca    1800 gatggccaag gataaagtca gtctgacctg catgataaca aacttcttcc ctgaagacat    1860
tactgtggag tggcagtgga atgggcagcc agcggagaac tacaagaaca ctcagcccat    1920
catggacaca gatggctctt acttcgtcta cagcaagctc aatgtgcaga gagcaactg     1980 ggaggcagga aatactttca cctgctctgt gttacatgag ggcctgcaca accaccatac    2040
tgagaagagc ctctcccact ctcctggtaa aactagtggc aaaccaatcc aaacccact    2100 gctgggcctg gatagtactt aaaagcttaa acccgctgat cagcctcgac tgtgccttct    2160
agttgccagc catctgttgt ttgcccctcc cccgtgcctt ccttgaccct ggaaggtgcc    2220
actcccactg tcctttccta ataaaatgag gaaattgcat cgcattgtct gagtaggtgt    2280
cattctattc tggggggtgg ggtggggcag gacagcaagg gggaggattg ggaagacaat    2340
```

```
agcaggcatg ctggggatgc ggtgggctct atggcttctg aggcggaaag aaccagctgg    2400
ggctctaggg ggtatcccca cgcgccctgt agcggcgcat taagcgcggc gggtgtggtg    2460
gttacgcgca gcgtgaccgc tacacttgcc agcgccctag cgcccgctcc tttcgctttc    2520
ttcccttcct ttctcgccac gttcgccggc tttccccgtc aagctctaaa tcggggggctc   2580 cctttagggt tccgatttag tgctttacgg cacctcgacc ccaaaaaact tgattagggt    2640
gatggttcac gtagtgggcc atcgcccga tagacggttt ttcgcccttt gacgttggag    2700
tccacgttct ttaatagtgg actcttgttc caaactggaa caacactcaa ccctatctcg    2760
gtctattctt ttgatttata agggattttg ccgatttcgg cctattggtt aaaaaatgag    2820
ctgatttaac aaaaatttaa cgcgaattaa ttctgtggaa tgtgtgtcag ttagggtgtg    2880
gaaagtcccc aggctcccca gcaggcagaa gtatgcaaag catgcatctc aattagtcag    2940
caaccaggtg tggaaagtcc ccaggctccc cagcaggcag aagtatgcaa agcatgcatc    3000
tcaattagtc agcaaccata gtcccgcccc taactccgcc catcccgccc ctaactccgc    3060
ccagttccgc ccattctccg ccccatggct gactaatttt ttttatttat gcagaggccg    3120
aggccgcctc tgcctctgag ctattccaga gtagtgagg aggcttttt ggaggcctag     3180 gcttttgcaa aaagctcccg ggagcttgta tatccatttt cggatctgat cagcacgtga    3240
tgaaaaagcc tgaactcacc gcgacgtctg tcgagaagtt tctgatcgaa aagttcgaca    3300
gcgtctccga cctgatgcag ctctcggagg gcgaagaatc tcgtgctttc agcttcgatg    3360
taggagggcg tggatatgtc ctgcgggtaa atagctgcgc cgatggtttc tacaaagatc    3420
gttatgttta tcggcacttt gcatcggccg cgctcccgat tccggaagtg cttgacattg    3480
gggaattcag cgagagcctg acctattgca tctcccgccg tgcacagggt gtcacgttgc    3540
aagacctgcc tgaaaccgaa ctgcccgctg ttctgcagcc ggtcgcgag gccatggatg    3600 cgatcgctgc ggccgatctt agccagacga gcgggttcgg cccattcgga ccgcaaggaa    3660
tcggtcaata cactacatgg cgtgatttca tatgcgcgat tgctgatccc catgtgtatc    3720
actggcaaac tgtgatggac gacaccgtca gtgcgtccgt cgcgcaggct ctcgatgagc    3780
tgatgctttg gccgaggac tgccccgaag tccggcacct cgtgcacgcg gatttcggct    3840
ccaacaatgt cctgacggac aatggccgca taacagcggt cattgactgg agcgaggcga    3900
tgttcgggga ttcccaatac gaggtcgcca acatcttctt ctggaggccg tggttggctt    3960
gtatggagca gcagacgcgc tacttcgagc ggaggcatcc ggagcttgca ggatcgccgc    4020
ggctccgggc gtatatgctc cgcattggtc ttgaccaact ctatcagagc ttggttgacg    4080
gcaatttcga tgatgcagct tgggcgcagg tcgatgcga cgcaatcgtc cgatccggag    4140
ccgggactgt cgggcgtaca caatcgcccg cagaagcgc ggccgtctgg accgatggct    4200
gtgtagaagt actcgccgat agtggaaacc gacgccccag cactcgtccg agggcaaagg    4260
aatagcacgt gctacgagat ttcgattcca ccgccgcctt ctatgaaagg ttgggcttcg    4320
gaatcgtttt ccgggacgcc ggctggatga tcctccagcg cggggatctc atgctggagt    4380
tcttcgccca ccccaacttg tttattgcag cttataatgg ttacaaataa agcaatagca    4440
tcacaaattt cacaaataaa gcatttttt cactgcattc tagttgtggt ttgtccaaac    4500
tcatcaatgt atcttatcat gtctgtatac cgtcgacctc tagctagagc ttggcgtaat    4560
catggtcata gctgtttcct gtgtgaaatt gttatccgct cacaattcca cacaacatac    4620
gagccggaag cataaagtgt aaagcctggg gtgcctaatg agtgagctaa ctcacattaa    4680
ttgcgttgcg ctcactgccc gctttccagt cgggaaacct gtcgtgccag ctgcattaat    4740
```

```
gaatcggcca acgcgcgggg agaggcggtt tgcgtattgg gcgctcttcc gcttcctcgc    4800
tcactgactc gctgcgctcg gtcgttcggc tgcggcgagc ggtatcagct cactcaaagg    4860
cggtaatacg gttatccaca gaatcagggg ataacgcagg aaagaacatg tgagcaaaag    4920
gccagcaaaa ggccaggaac cgtaaaaagg ccgcgttgct ggcgtttttc cataggctcc    4980
gcccccctga cgagcatcac aaaaatcgac gctcaagtca gaggtggcga acccgacag     5040
gactataaag ataccaggcg tttccccctg gaagctccct cgtgcgctct cctgttccga    5100
ccctgccgct taccggatac ctgtccgcct ttctcccttc gggaagcgtg gcgctttctc    5160
atagctcacg ctgtaggtat ctcagttcgg tgtaggtcgt tcgctccaag ctgggctgtg    5220
tgcacgaacc ccccgttcag cccgaccgct gcgccttatc cggtaactat cgtcttgagt    5280
ccaacccggt aagacacgac ttatcgccac tggcagcagc cactggtaac aggattagca    5340
gagcgaggta tgtaggcggt gctacagagt tcttgaagtg gtggcctaac tacggctaca    5400
ctagaagaac agtatttggt atctgcgctc tgctgaagcc agttaccttc ggaaaaagag    5460
ttggtagctc ttgatccggc aaacaaacca ccgctggtag cggtttttttt gtttgcaagc    5520
agcagattac gcgcagaaaa aaaggatctc aagaagatcc tttgatcttt tctacggggt    5580
ctgacgctca gtggaacgaa aactcacgtt aagggatttt ggtcatgaga ttatcaaaaa    5640
ggatcttcac ctagatcctt ttaaattaaa aatgaagttt taaatcaatc taaagtatat    5700
atgagtaaac ttggtctgac agttaccaat gcttaatcag tgaggcacct atctcagcga    5760
tctgtctatt tcgttcatcc atagttgcct gactccccgt cgtgtagata actacgatac    5820
gggagggctt accatctggc cccagtgctg caatgatacc gcgagaccca cgctcaccgg    5880
ctccagattt atcagcaata aaccagccag ccggaagggc cgagcgcaga agtggtcctg    5940
caactttatc cgcctccatc cagtctatta attgttgccg ggaagctaga gtaagtagtt    6000
cgccagttaa tagtttgcgc aacgttgttg ccattgctac aggcatcgtg gtgtcacgct    6060
cgtcgtttgg tatggcttca ttcagctccg gttcccaacg atcaaggcga gttacatgat    6120
cccccatgtt gtgcaaaaaa gcggttagct ccttcggtcc tccgatcgtt gtcagaagta    6180
agttggccgc agtgttatca ctcatggtta tggcagcact gcataattct cttactgtca    6240
tgccatccgt aagatgcttt tctgtgactg gtgagtactc aaccaagtca ttctgagaat    6300
agtgtatgcg gcgaccgagt tgctcttgcc cggcgtcaat acgggataat accgcgccac    6360
atagcagaac tttaaaagtg ctcatcattg gaaaacgttc ttcggggcga aaactctcaa    6420
ggatcttacc gctgttgaga tccagttcga tgtaacccac tcgtgcaccc aactgatctt    6480
cagcatcttt tactttcacc agcgtttctg ggtgagcaaa acaggaagg caaaatgccg    6540
caaaaaaggg aataagggcg acacggaaat gttgaatact catactcttc cttttttcaat   6600
attattgaag catttatcag ggttattgtc tcatgagcgg atacatattt gaatgtattt    6660
agaaaaataa acaaataggg gttccgcgca catttccccg aaaagtgcca cctgacgtc    6719
```

<210> SEQ ID NO 11
<211> LENGTH: 9
<212> TYPE: DNA
<213> ORGANISM: artificial
<220> FEATURE:
<223> OTHER INFORMATION: Kozak sequence

<400> SEQUENCE: 11 ccaccatgg                                                              9

```
<210> SEQ ID NO 12
<211> LENGTH: 41
<212> TYPE: DNA
<213> ORGANISM: artificial
<220> FEATURE:
<223> OTHER INFORMATION: secretory leader sequence

<400> SEQUENCE: 12
gctggagcct gatcctcctg ttcctcgtcg ctgtggctac a          41

<210> SEQ ID NO 13
<211> LENGTH: 84
<212> TYPE: DNA
<213> ORGANISM: artificial
<220> FEATURE:
<223> OTHER INFORMATION: mini intron seq

<400> SEQUENCE: 13
ggtaaggggc tcacagtagc aggcttgagg tctggacata tatgggtg acaatgacat    60 cctttgcctt tctctccaca ggtg                                         84

<210> SEQ ID NO 14
<211> LENGTH: 42
<212> TYPE: DNA
<213> ORGANISM: artificial
<220> FEATURE:
<223> OTHER INFORMATION: tag sequence

<400> SEQUENCE: 14
ggcaaaccaa tcccaaaccc actgctgggc ctggatagta ct         42

<210> SEQ ID NO 15
<211> LENGTH: 32
<212> TYPE: DNA
<213> ORGANISM: artificial
<220> FEATURE:
<223> OTHER INFORMATION: primer

<400> SEQUENCE: 15
ttggcgcgca tgccgaaatc aatggttctg cc                    32

<210> SEQ ID NO 16
<211> LENGTH: 31
<212> TYPE: DNA
<213> ORGANISM: artificial
<220> FEATURE:
<223> OTHER INFORMATION: primer

<400> SEQUENCE: 16
ctagctagca agttgtgatt cataaatatg c                     31

<210> SEQ ID NO 17
<211> LENGTH: 29
<212> TYPE: DNA
<213> ORGANISM: artificial
<220> FEATURE:
<223> OTHER INFORMATION: primer

<400> SEQUENCE: 17
ttggcgcgca tgccgaaatc aatggctcg                        29

<210> SEQ ID NO 18
<211> LENGTH: 29
<212> TYPE: DNA
<213> ORGANISM: artificial
```

```
<220> FEATURE:
<223> OTHER INFORMATION: primer

<400> SEQUENCE: 18
ctagctagct agccagagct tcagctggc                                        29

<210> SEQ ID NO 19
<211> LENGTH: 18
<212> TYPE: DNA
<213> ORGANISM: artificial
<220> FEATURE:
<223> OTHER INFORMATION: primer

<400> SEQUENCE: 19
ctgcttactg gcttatcg                                                    18

<210> SEQ ID NO 20
<211> LENGTH: 18
<212> TYPE: DNA
<213> ORGANISM: artificial
<220> FEATURE:
<223> OTHER INFORMATION: primer

<400> SEQUENCE: 20
cagatggctg gcaactag                                                    18

<210> SEQ ID NO 21
<211> LENGTH: 25
<212> TYPE: DNA
<213> ORGANISM: artificial
<220> FEATURE:
<223> OTHER INFORMATION: siRNA B7h

<400> SEQUENCE: 21
cagcagccuu cgagcugaua cucag                                            25

<210> SEQ ID NO 22
<211> LENGTH: 25
<212> TYPE: DNA
<213> ORGANISM: artificial
<220> FEATURE:
<223> OTHER INFORMATION: siRNA B7h

<400> SEQUENCE: 22
cugaguauca gcucgaaggc ugcug                                            25

<210> SEQ ID NO 23
<211> LENGTH: 25
<212> TYPE: DNA
<213> ORGANISM: artificial
<220> FEATURE:
<223> OTHER INFORMATION: siRNA B7h

<400> SEQUENCE: 23
ggcccaacgu guacuggauc aauaa                                            25

<210> SEQ ID NO 24
<211> LENGTH: 25
<212> TYPE: DNA
<213> ORGANISM: artificial
<220> FEATURE:
<223> OTHER INFORMATION: siRNA B7h

<400> SEQUENCE: 24
uuauugaucc aguacacguu gggcc                                            25
```